United States Patent [19]

Loh

[11] Patent Number: 4,497,649
[45] Date of Patent: Feb. 5, 1985

[54] 5-O-ACYL-5-C-ALKYL-3-O-ARYLMETHYL OR SUBSTITUTED ARYLMETHYL-1,2-O-ALKYLIDENE-αD-GLUCO-PENTOFURANOSE AND β-L-IDO-PENTOFURANOSE HERBICIDES

[75] Inventor: William Loh, Petaluma, Calif.

[73] Assignee: Chevron Research Company, San Francisco, Calif.

[21] Appl. No.: 524,512

[22] Filed: Aug. 18, 1983

[51] Int. Cl.³ .................. A01N 43/08; C07H 17/04
[52] U.S. Cl. ............................. 71/88; 536/4.1; 536/18.1; 536/18.2
[58] Field of Search ............. 536/4.1, 18.1, 18.2; 424/180; 71/88

[56] References Cited

U.S. PATENT DOCUMENTS

| | | | |
|---|---|---|---|
| 3,586,664 | 6/1971 | Kohno et al. | 536/18.2 |
| 3,919,252 | 11/1975 | Barker et al. | 260/340.9 |
| 4,004,911 | 1/1977 | Isaac et al. | 71/88 |
| 4,116,669 | 9/1978 | Barker et al. | 71/88 |
| 4,146,384 | 3/1979 | Schmidt et al. | 71/88 |
| 4,207,088 | 6/1980 | Konz | 71/88 |
| 4,330,320 | 5/1982 | Baker | 71/94 |

FOREIGN PATENT DOCUMENTS

| | | | |
|---|---|---|---|
| 0000002 | of 0000 | European Pat. Off. | |
| 0154992 | 12/1980 | Japan | 536/4.1 |

OTHER PUBLICATIONS

J. Org. Chem., 27, 2107, (1962).
Chem. Ber, 102, 820, (1969).
Helv. Chim. Acta, 56, 1802, (1973).
Carbohydrate Research, 31, (1973), pp. 387–396.
Bulletin of the Chem. Society of Japan, 51, (12), (1978).
Carbohyd. Res., 7, 161, (1968).
J. Amer. Chem. Soc., 78, 2846, (1956).
Methods in Carbohyd. Chem., vol. VI, 297, (1972).
Tetrahedron Letters, No. 26, pp. 2447–2448, (1979).
Tetrahedron Letters, No. 35, pp. 3233–3236, (1978).
J. Chem. Soc. Jap., Chem. Ind. Chem., 1981, (5), 769–775, Chem. Absts.
Synthesis, 636, (1980).
Helv. Chem. Acta, 56.
J. Chem. Soc., Perkin Trans I., 38, (1973).
J. of Organic Chemistry, 46, (1981), pp. 1296–1309.
J. of Organic Chemistry, 44, (1979), pp. 4294–4299.
Carbohydrate Research, 29, (1973), pp. 311–323.

Primary Examiner—Johnnie R. Brown
Assistant Examiner—Elli Peseler
Attorney, Agent, or Firm—S. R. LaPaglia; T. G. DeJonghe; L. S. Squires

[57] ABSTRACT

5-O-acyl-5-C-alkyl-3-O-substituted arylmethyl-1,2-O-alkylidene-α-D-gluco- and β-L-ido-pentofuranoses. The compounds exhibit herbicidal activity and especially pre-emergence herbicidal activity against grasses.

20 Claims, No Drawings

5-O-ACYL-5-C-ALKYL-3-O-ARYLMETHYL OR SUBSTITUTED ARYLMETHYL-1,2-O-ALKYLIDENE-αD-GLUCO-PENTOFURANOSE AND β-L-IDO-PENTOFURANOSE HERBICIDES

BACKGROUND OF THE INVENTION

This invention relates to 5-C-alkyl-3-O-arylmethyl and substituted arylmethyl-1,2-O-alkylidene-α-D-xylo-pentodialdofuranose, α-D-gludo- and β-L-ido-pentofuranose derivatives and to the application of such compounds as herbicides and plant growth regulators. The invention also relates to the preparation of such compounds.

5-O-acetyl-1,2-isopropylidene-3-O-(4-methoxybenzyl)-6-deoxy-α-D-glucofuranose is described in Tetrahedran Letters, Vol. 23, No. 8, pp. 885–888 (1982) to illustrate the removal of O-p-methoxybenzyl protecting groups via DDQ oxidation.

The laboratory preparation of 3-O-benzyl-6,7-dideoxy-1,2-O-isopropylidene-α-D-xylo-heptofuranos-5-ulose and/or 3-O-benzyl-6-deoxy-1,2-O-isopropylidene-α-D-xylohexofuranos-5-ulose for academic studies is described in Carbohydrate Research 31 (1973), pages 387–396; Carbohydrate Research 29 (1973), pages 311–323; Bulletin of the Chemical Society of Japan, 51 (12) (1978), pages 3595–3598; Journal of Organic Chemistry 44 (1979), pages 4294–4299; Journal of Organic Chemistry 46, (1981), pages 1296–1309; Journal of Organic Chemistry 27, 2107 (1962); Chem. Ber. 102, 820 (1969); Carbohydrate Research 26, 441 (1973); and Helv. Chem. Acta. 56, 1802 (1973).

U.S. Pat. Nos. 4,116,669, 4,146,384 and 4,330,320 and German Pat. No. DS 2,860,975 disclose a broad range of tetrahydrofuran derivatives and attribute herbicidal activity to these derivatives. U.S. Pat. Nos. 3,919,252, 4,004,991 and 4,207,088 disclose dioxalane derivatives and dioxane derivatives and attribute grass herbicidal activity to these derivatives. The sodium salt of 2,3:4,6-bis-O-(1-methylethylidene)-O-(L-xylo-2-hexulofuranosonic acid) is sold as a pinching agent for azaleas and ornamentals and a growth retardant for shrubs, hedges and ground covers and is disclosed in U.S. Pat. No. 4,007,206.

The application of 5-C-alkyl-3-O-benzyl-1,2-O-isopropylidene α-D-xylo-pentodialdofuranose as herbicides and plant growth regulators is described by B. McCaskey in commonly assigned copending application Ser. No. 387,590 filed June 11, 1982.

In my prior co-pending application Ser. No. 409,236, filed Aug. 18, 1982 now allowed U.S. Pat. No. 4,429,119, I disclosed certain 5-deoxy-3-O-arylmethyl or substituted arylmethyl-1,2-O-alkylidene-α-D-xylofuranose derivatives which are useful as herbicides and plant growth regulators. In my copending application Ser. No. 489,981, filed Apr. 29, 1983, I disclose certain 5-C-alkyl-3-O-arylmethyl or substituted arylmethyl-1,2-O-alkylidene-α-D-xylo-pentodialdofuranose and α-D-gluco-and β-L-ido-pentofuranose derivatives which are also generally useful as herbicides.

SUMMARY OF THE INVENTION

The present invention provides compounds having herbicidal activity and plant growth regulating activity and provides method and compositions for preventing or retarding unwanted vegetation and for controlling the growth of vegetation. Certain of the active compounds are composed only of hydrogen, oxygen and carbon and hence are very desirable from an environmental standpoint because they decompose into innocuous carbon-oxygen moieties and water. Certain compounds of the invention also exhibit increased phytotoxic selectivity and crop safety. Also, as pointed out in my aforementioned patent application, I have found that biological activity in tetrahydrofuranyl nucleous compounds is very unpredictable and requires the proper stereo-configuration. For example, even though the compounds and compositions of the present invention exhibit very good herbicide activity, especially grass pre-emergence herbicide activity, and plant growth regulating activity, a number of closely related analogs and even the 3-epimers of the present compounds fail to exhibit such activity.

In one aspect the invention provides compounds having the formula

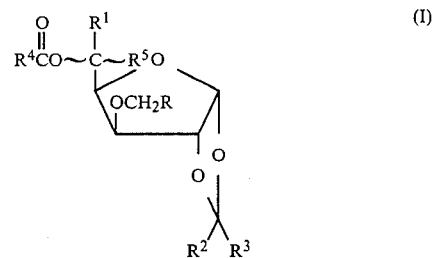

wherein

R is naphthyl, phenyl, 2-trifluoromethylphenyl; or substituted aryl having 6 through 10 carbon atoms and 1 through 3 substituents independently selected from the group of lower alkyl, and halo;

$R^1$ is alkyl having 1 through 4 carbon atoms;

$R^2$ and $R^3$ are independently selected from the group consisting of hydrogen; lower alkyl; lower haloalkyl having 1 through 3 halo substituents; and aryl having 6 through 10 carbon atoms; or $R^2$ and $R^3$ together with the carbon atom to which they are joined form a cycloalkyl group having 5 or 6 carbon atoms;

$R^4$ is lower alkyl, lower alkoxyalkyl, lower haloalkyl, aryl or substituted aryl having 1 through 3 ring substituents independently selected from the group of lower alkyl, lower alkoxy, halo, and trifluoromethylphenyl; and $R^5$ is hydrogen or methyl.

The compounds of Formula I are (D) optically active and can comprise various isomers provided that the orientation of the substituents at the 1, 2, 3 and 4 positions relative to each other with respect to the furan ring must be as shown in Formula I. The wavy bond lines (∼) indicate that the ester group (—OOCR$^4$) can be oriented as D-gluco or L-ido or can be a mixture of these isomers. Formula (I) is intended to represent the respective pure isomers as well as mixtures thereof, having the relative orientations at the 1, 2, 3 and 4 positions shown in Formula (I) and both the respective individual isomers and isomer mixtures are encompassed within the invention. The compounds of Formula I exhibit herbicidal activity.

In a further aspect the invention provides a herbicidal composition comprising a compatible carrier and a herbicidally effective amount of the compounds of formula I or mixtures thereof.

The present invention also provides a method for preventing or controlling the growth of unwanted vegetation, especially grasses, which comprises treating the growth medium and/or the foliage of such vegetation with a herbicidally effective amount of the compound(s) of Formula I.

In another aspect, the present invention provides a plant growth regulating composition comprising a carrier and an effective amount of the plant growth regulating compound(s) of the Formula I.

The present invention also provides a method for regulating plant growth which comprises treating the growth medium and/or the foliage of such vegetation with a plant growth regulating effective amount of the compound(s) of Formula I.

The present invention also provides chemical intermediates and processes for preparing the compounds of Formula I.

The invention will be further described hereinbelow.

FURTHER DESCRIPTION OF THE INVENTION AND THE PREFERRED EMBODIMENTS

In terms of the D-gluco and L-ido isomers, the compounds of the present invention can be represented by the following formulas:

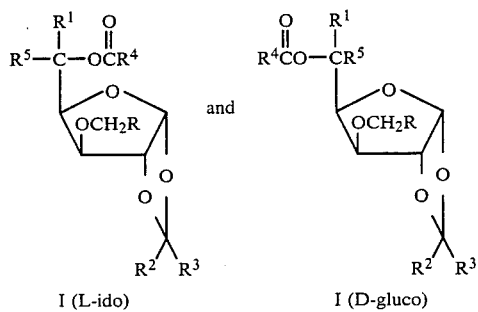

I (L-ido)      I (D-gluco)

wherein R, $R^1$, $R^2$, $R^3$, $R^4$ and $R^5$ are as defined hereinabove.

Illustrations of typical compounds of Formula (I) of the present invention can be had by reference to Examples 9 and 10 set forth hereinbelow on pages 35 and 45. In terms of substituents the preferred compounds for herbicidal activity, cost effectiveness and/or selectivity are those wherein $R^1$ is methyl or ethyl, and/or $R^5$ is hydrogen. The preferred R substituents are monosubstituted aryls, preferably monosubstituted phenyl, having a single substituent selected from the group lower alkyl, (preferably methyl) lower alkoxy (preferably methoxy) and halo (preferably chloro or fluoro). Preferably, $R^4$ is lower alkyl or lower haloalkyl, more preferably methyl or chloromethyl, or phenyl. Preferably, $R^5$ is hydrogen. More preferably, R is monosubstituted phenyl substituted at the 2-position and especially 2-halophenyl, and more especially 2-chlorophenyl. Preferably, $R^2$ and $R^3$ are independently hydrogen, methyl or ethyl and more preferably $R^2$ and $R^3$ are each methyl.

The compounds of Formula I of the present invention can be prepared via esterification of the corresponding alcohols:

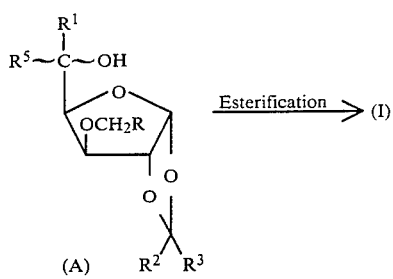

wherein R, $R^1$, $R^2$, $R^3$, $R^4$ and $R^5$ are as defined hereinabove.

Preferably, the esterification is conducted by contacting the compound of formula (A) with an acylating agent having the appropriate $R^4$ substituent, such as, for example, the appropriate acyl chloride or bromide ($R^4C(O)X$; where X is Cl or Br) or carboxylic acid anhydride (($R^4C=O)_2O$).

Where acyl halides are used, this reaction can be conveniently conducted by contacting compound A with the acyl halide, preferably in an inert organic solvent and in the presence of a scavenger base. Typically, this reaction is conducted at temperatures in the range of about from −78 and 100, preferably 0° to 25° C., for about from 1 to 48 hours, preferably 5 to 12 hours, using about from 1 to 5, preferably 1 to 1.2 moles of acyl halide per mole of compound (A). Suitable inert organic solvents which can be used include, for example, ethyl acetate, methylene chloride, chloroform, diethyl ether, and the like and compatible mixtures thereof. Where a scavenger base is used typically about from 1 to 2 moles of base are used per mole of compound A. Suitable scavenger bases which can be used include, for example, pyridine, triethylamine, methylpyridine, and the like.

In the case where carboxylic acid anhydride is used, the reaction can be conveniently conducted by contacting compound A with the anhydride, preferably in the presence of a scavenger base and optionally in an inert organic solvent. Typically, this reaction is conducted at temperatures in the range of about from −78 to 100, preferably 0° to 25° C., for about from 1 to 48 hours, preferably 5 to 12 hours, using about from 1 to 5, preferably 1 to 1.2 moles of anhydride per mole of compound (A). Suitable inert organic solvents which can be used include, for example, ethyl acetate, methylene chloride, chloroform, diethyl ether, and the like and compatible mixtures thereof. Where a scavenger base is used typically about from 1 to 2 moles of base are used per mole of compound A. Suitable scavenger bases which can be used include, for example, pyridine, triethylamine, methylpyridine, and the like.

The starting material of Formula A wherein $R^5$ is hydrogen can be prepared by treating the corresponding 5-aldehyde precursor with the appropriate alkyl Grignard reagent. This can be schematically represented by the following overall reaction equation:

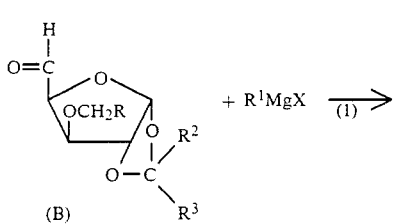

(B)

+ R¹MgX $\xrightarrow{(1)}$

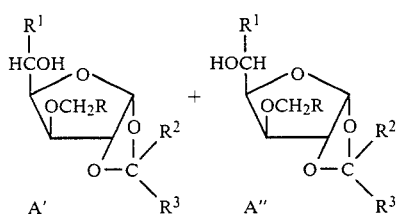

A'    A"

wherein X is halo, preferably bromo or iodo; R and R¹, are as defined hereinabove, and $R^6$ and $R^7$ are as defined hereinabove for $R^2$ and $R^3$, respectively, but both are not hydrogen.

This process can be effected by contacting the aldehyde (B) with a Grignard reagent, having the appropriate R¹ group, preferably in an inert organic solvent (preferably, ethyl ether). This step is typically conducted at temperatures in the range of about from 0° to 35° C., and conveniently is conducted by refluxing the reaction mixture for about from 1 to 10 hours. Suitable solvents which can be used include, for example, lower alkyl ethers (e.g., ethyl ether, propyl ether, butyl ether); tetrahydrofuran; methyltetrahydrofuran; dioxane, dimethoxymethane, dimethoxybutane, and the like and compatible mixtures thereof. Suitable Grignard reagents which can be used include, for example, ethylmagnesium bromide, ethylmagnesium iodide, methylmagnesium bromide, methylmagnesium iodide, propylmagnesium chloride, and the like. Typically, about from 2 to 20, preferably 6 to 10, mole equivalents of Grignard reagent is used per mole of compound B. The resulting reaction product is a mixture of diastereoisomeric alcohols A' and A" which can be used as a mixture or if desired the respective isomers A' and A" can be separated via any suitable procedure, for example, via crystallization or chromatography, etc.

The compounds of Formula A wherein $R^5$ is methyl and $R^2$ and/or $R^3$ are other than hydrogen can be prepared via reaction of the corresponding ketone with a methyl Grignard reagent.

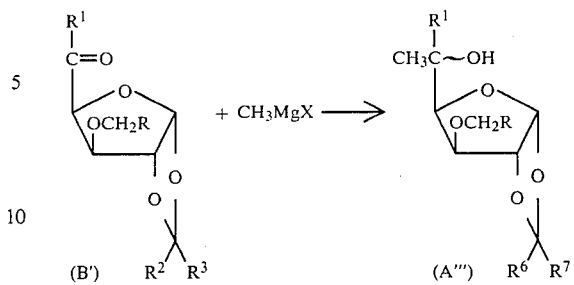

(B''')    (A''')

wherein R, R¹, R², R³ and the wavy line (∼) are as defined hereinabove and X is halo, preferably chloro or bromo.

This reaction can be conveniently conducted in the same manner as described hereinabove with respect to the Grignard alkylation of compound B. Compound A''' can conveniently be acylated directly to compound (I).

The starting materials of formula B' can be prepared via oxidation of the corresponding compounds A' and/or A". This can be schematically represented by the following overall reaction equation:

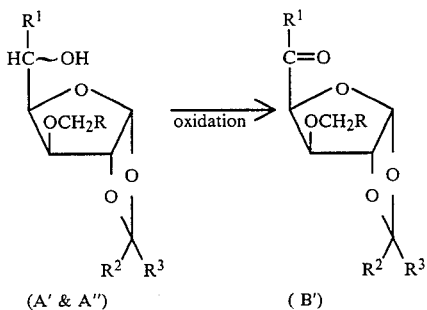

(A' & A")    (B')

wherein R, R¹, R² and R³ are as defined as hereinabove, and the wavy line (∼) indicates that the OH group may be oriented as the D-gluco or L-ido configuration.

The oxidation step can be conveniently effected by contacting compound Ia" with a suitable oxidizing reagent (preferably, Jones reagent, i.e., $H_2CrO_4$) preferably in an inert organic solvent (preferably acetone).

Typically, this step is conducted at temperatures in the range of about from −80° to 55° C., preferably about from −60° to 25° C. for about from 1 to 10 hours. Suitable inert organic solvents which can be used for this reaction include, for example, acetone, benzene, ether, acetic acid-water, pyridine, and the like. Suitable oxidation reagents which can be used include, for example, methyl sulfoxide, chromium trioxide, sodium dichromate, potassium dichromate, and the like. Typically about from 1 to 5 mole equivalents of oxidizing agent are used per mole of compound (A'+A"). Compound (B') can be separated from the reaction product via any suitable procedure, for example, chromatographically.

The starting materials of formula B can be prepared via the following schematically represented overall reaction sequence:

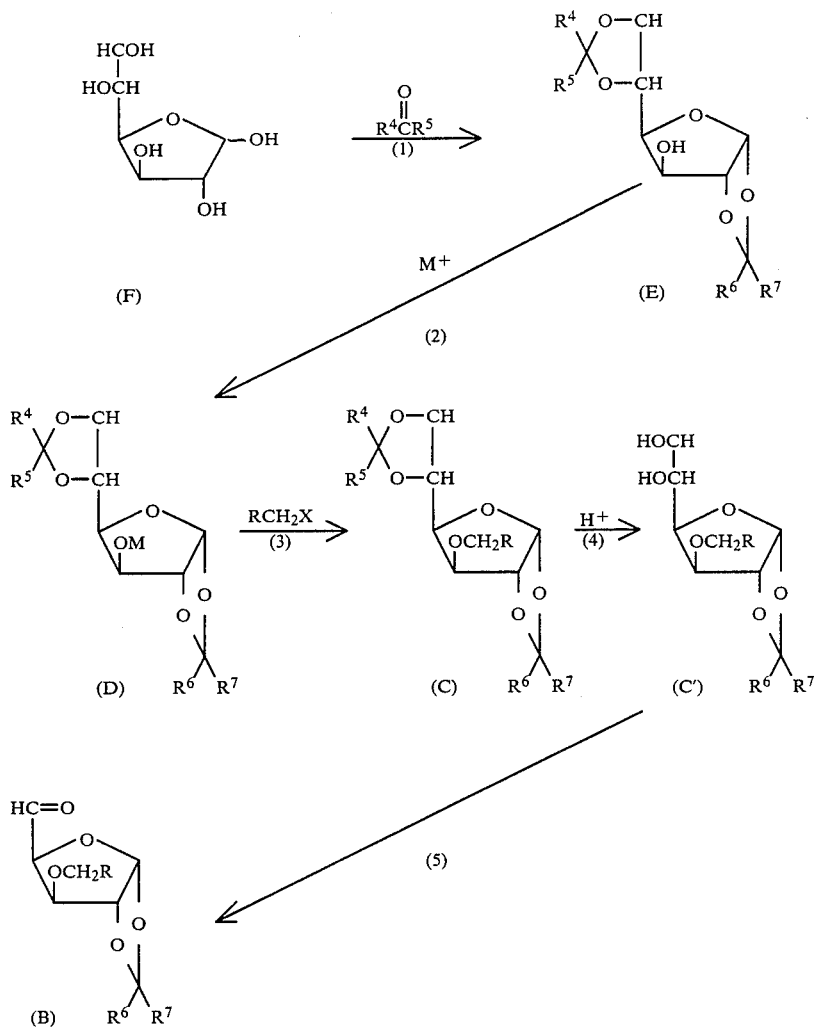

wherein R, is as defined hereinabove; $R^6$ and $R^7$ are independently lower alkyl, lower haloalkyl having 1 through 3 halo substituents or aryl having 6 through 10 carbon atoms or $R^6$ and $R^7$ together with the carbon atoms to which they are joined, form a cycloalkyl group having 5 or 6 carbon atoms; M is an alkali metal cation; X is chloro, bromo, or iodo; and the wavy line indicates that the hydroxy group can be either α or β.

The first step of this process can be conveniently effected by reacting the pentahydroxy alcohol of formula F (i.e. glucose) with the appropriate $R^4R^5$ ketone, for example, as disclosed in Advan. Carbohydrate Chem. 20, 219 (1965). For example, using acetone, preferably in an excess amount and which also acts as the organic solvent, and in the presence of a small amount of an acid catalyst will yield the compound of formula (E) wherein $R^4$ and $R^5$ are each methyl; note, for example, Methods in Carbohyd. Chem., 2, 320 and 321 (1966). Similarly using cyclohexanone as the $R^4$, $R^5$ ketone will yield the compound of formula E wherein $R^4$ and $R^5$ together with the carbon atoms to which they are joined form a cyclohexane ring, for example, as described in J. Amer. Chem. Soc., 71 3072 (1949).

Typically step 1 is conducted at temperatures in the range of about from 0° to 50° C., preferably 10° to 25° C. for about from 1 to 48 hours, preferably 5 to 24 hours using a stoichiometric excess of ketone which also acts as solvent when the ketone is a liquid. Also, in place of, or together with, using excess ketone as the solvent other suitable inert organic solvents could also be used. Suitable organic solvents which can be used include, for example, ether, benzene, DMF, p-dioxane, and the like and compatible mixtures thereof. Suitable acid catalysts which can be used include, for example, concentrated sulfuric acid, hydrogen chloride, zinc chloride-phosphoric acid, ferric chloride, and the like. Typically, a catalyst concentration in the reaction mixture of about from 0.1 to 5 weight percent is used.

The second step of the reaction sequence can be effected by contacting Compound E with an alkali metal base such as sodium hydride, potassium hydride, sodium hydroxide, potassium hydroxide, and the like, preferably in an inert organic solvent. Typically, this reaction is conducted at about from 0 to the following point of the solvent, preferably about from 0° to 65° C., for about from 0.5 to 12 hours, preferably 0.5 to 1 hour, using about from 1.0 to 1.1 moles of alkali metal base per mole of Compound E. Conveniently the third step of the reaction sequence can be conducted in situ. Accordingly, the same solvents as are indicated below for the third step are conveniently used for this step.

The third step of the reaction sequence can be effected by contacting Compound D with the desired R substituted arylmethyl halide, preferably a chloride or bromide, preferably in an inert organic solvent (e.g., tetrahydrofuran) and in the presence of an appropriate catalyst. This process is typically conducted at temperatures in the range of about from 0 to the boiling point of the solvent, preferably about from 25° to 75°, for about from 1 to 48 hours, preferably about from 3 to 12 hours. Typically, from about 1.0 to 1.25 moles, and preferably about from 1.0 to 1.1 moles of substituted arylmethyl halide is used per mole of Compound D.

Suitable inert organic solvents which can be used include, for example, tetrahydrofuran, ethyl ether, xylene, toluene, dimethylsulfoxide, dimethylformamide, and the like and compatible mixtures thereof. Suitable catalysts which can be used include, for example, tetrabutylammonium iodide, tetrabutylammonium bromide, benzyltriethylammonium chloride, tricaprylyl methylammonium chloride and the like. Typically, a catalyst to reactant (D) ratio of about from 0.01 to 0.1 mole of catalyst per mole of D is used. Generally, best results are obtained using tetrahydrofuran as the solvent, tetrabutylammonium iodide as the catalyst and conducting the reaction at about from 25° to 65° C. for about from 3 to 12 hours.

Compound C wherein $R^4$ or $R^5$ is hydrogen can be prepared by complete hydrolysis of the 1,2:5,6-di-O-alkylidene groups of Compound C wherein $R^4$ and $R^5$ are alkyl by using longer reaction times and higher reaction temperatures as are indicated below in the fourth step followed by diacetalation with the appropriate aldehyde as described hereinabove in step 1.

In the fourth step the 5,6-O-alkylidene group is selectively cleaved without cleaving the 1,2-O-alkylidene group. This can be conveniently effected by mild acid hydrolysis, for example, by contacting Compound C with aqueous acetic acid at temperatures in the range of about from 25° to 100° C.; preferably about from 40° to 60° C. for about from 1 to 48 hours. The hydrolysis can also be conducted, for example, in aqueous trifluoroacetic acid, aqueous hydrochloric acid, and the like, and compatible mixtures thereof.

The fifth step, oxidative cleavage and displacement of the 6 position carbon group, can be effected by contacting Compound C' with an alkali metal metaperiodate (e.g., sodium metaperiodate) or lead tetraacetate preferably in an inert organic solvent. Typically, this process is conducted at temperatures in the range of about from 0° to 70° C., preferably 0° to 30° C. using about from 1.0 to 1.25 moles of alkali metal metaperiodate per mole of Compound C'. Suitable solvents which can be used include, for example, tetrahydrofuran, methanol, benzene, toluene, water, and the like.

The starting materials of formula B wherein one or both of $R^2$ and/or $R^3$ are hydrogen can in theory be prepared via the reaction sequence described above by replacing the ketone in step 1 (F to E) with the appropriate aldehyde. However, in practice, because of interfering reactions, these compounds and also the compounds of formula B' are best prepared as follows:

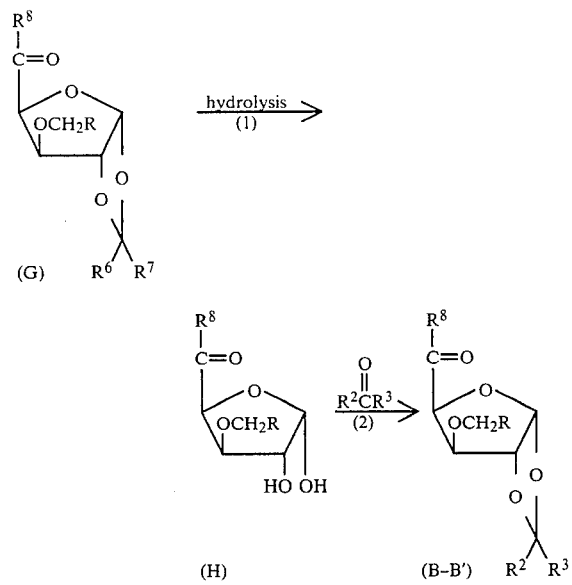

wherein R, $R^1$, $R^2$, $R^3$, $R^6$, $R^7$ and Z are as defined hereinabove and $R^8$ is hydrogen or alkyl having 1 through 4 carbon atoms.

In the first step of this reaction sequence the $R^6$, $R^7$ acetal group is removed by mild acid hydrolysis. This can be conveniently effected, for example, by contacting the Compound Ib (preferably $R^6$ and $R^7$ are lower alkyl and more preferably are each methyl) with aqueous trifluoroacetic acid, preferably at room temperature (about 20°–25° C.) for about 0.5–5 hours. The hydrolysis can also for example be conducted in aqueous acetic acid, aqueous hydrochloric acid, and the like, and compatible mixtures thereof.

The second step can be effected by contacting Compound H with a ketone, aldehyde, ketone-acetal, or aldehyde-acetal having the desired $R^2$, $R^3$ groups, preferably in the presence of a dehydrating agent and an acid catalyst. For example, the compound of formula I wherein one of $R^2$ or $R^3$ is hydrogen and the other is methyl can be prepared by using acetaldehyde. The compounds of formula I wherein $R^2$ and $R^3$ are each hydrogen can be prepared by using paraformaldehyde and can be prepared in a single in situ step by contacting Compound Id with paraformaldehyde and glacial acetic acid, followed by contact with a small amount of a strong acid (e.g., concentrated sulfuric acid) at about room temperature for about 0.5–5 hours.

The second step of this reaction is typically conducted at temperatures in the range of about from 25° C. to the boiling point of the ketone or aldehyde for about from 1 to 24 hours using about from 1 to 10 moles of aldehyde, ketone, aldehyde-acetal, or ketone-acetal per mole of Compound A' in the presence of a catalytic amount of acid (e.g., concentrated sulfuric acid or p-toluenesulfonic acid) and a dehydrating agent such as anhydrous copper sulfate, or molecular sieves.

It should also be apparent that general variation in the $R^2$ and $R^3$ groups can be effected by this procedure by first cleaving the existing $R^2$ and $R^3$ acetal group followed by reaction with the desired ketone, aldehyde, ketone-acetal, or aldehyde-acetal, under the condition described in step 2 above. In some instances this may be a more convenient method of even preparing the compounds wherein $R^2$ and $R^3$ are other than methyl because diacetone D-glucose is a commercially available starting material (i.e., Compound E, wherein $R^6$ and $R^7$ are methyl).

Also, if desired, by applying this procedure to the compounds of formula I, variations in the $R^2$ and/or $R^3$ can be effected.

GENERAL PROCESS CONDITIONS

In the above-described processes, it is generally preferable to separate the respected products before proceeding with the next step in the reaction sequence, except where described as an in situ step or unless otherwise expressly stated. These products can be recovered from their respective reaction product mixtures by any suitable separation and purification procedure, such as, for example, recrystallization and chromatography. Suitable separation and purification procedures are, for example, illustrated in the Examples set forth hereinbelow.

Generally, the reactions described above are conducted as liquid phase reaction and hence pressure is generally not significant except as it affects temperature (boiling point) where reactions are conducted at reflux. Therefore, these reactions are generally conducted pressures of from 300 to 3,000 mm of mercury and conveniently are conducted at about atmospheric or ambient pressure.

It should also be appreciated that where typical or preferred process conditions (e.g., reaction temperatures, times, mol ratios of reactants, solvents, etc.) have been given, that other process conditions could also be used, although typically with poorer yields or economies. Optimum reaction conditions (e.g., temperature, reaction time, mol ratios, solvents, etc.) may vary with the particular reagents or organic solvents used but can be determined by routine optimization procedures.

Where optical isomer mixtures are obtained, the respective optical isomers can be obtained by conventional resolution procedures, for example, by converting the isomer mixture to an acid derivative and reacting with an optically active base which will yield a mixture of optical salts, of the desired compound, which can be resolved by conventional procedures (e.g., crystallization) into the respective plus and minus optical salts.

Definitions

As used herein the following terms have the following meanings unless expressly stated to the contrary:

The term "lower alkyl" refers to both straight- and branched-chain alkyl groups having a total of from 1 through 4 carbon atoms and includes primary, secondary and tertiary alkyl groups. Typical lower alkyls include, for example, methyl, ethyl, n-propyl, isopropyl, n-butyl, t-butyl.

The term "lower alkoxy" refers to the group having the formula R'O— wherein R' is lower alkyl.

The term "lower alkoxyalkyl" refers to the group R'OR"— wherein R' and R" are independently lower alkyl. Preferably, such lower alkoxyalkyl groups have 2 through 8 carbon atoms. Typical alkoxyalkyl groups include, for example, methoxymethyl, 2-ethoxypropyl, hexoxybutyl, and the like.

The term "lower alkenyl" refers to alkenyl groups having 2 through 4 carbon atoms and includes for example vinyl; 1-propenyl, 2-propenyl, 1-methylvinyl, 1-butenyl, 2-methylprop-1-enyl and the like.

The term "halo" refers to the group of fluoro, chloro, bromo and iodo.

The term "lower haloalkyl" refers to haloalkyl groups having 1 through 6 carbon atoms and 1 through 3 halo atoms.

The term "aryl" refers to aryl groups having 6 through 10 carbon atoms and includes, for example, phenyl, naphthyl, indenyl, and the like.

The term "substituted aryl" refers to aryl groups having 6 through 10 carbon ring atoms and 1 through 4 substituents independently selected from the group of lower alkyl, lower alkoxy and halo. Typical substituted aryl includes, for example, 2-fluorophenyl, 2-chlorophenyl, 2,6-dimethylphenyl, 2-methylphenyl, 2,4-dimethylphenyl, 2,5-dimethylphenyl, 2,4-dichlorophenyl, 2-methoxyphenyl and the like.

The term "room temperature" or "ambient temperature" refers to about 20°–25° C.

UTILITY

The compounds of Formula I exhibit pre-emergence and also to a lesser extent post-emergence herbicide activity and exhibit especially good pre-emergence grass herbicide activity. The preferred herbicidal compounds of Formula (I) are those wherein $R^1$ is methyl or ethyl and especially the compound wherein $R^1$ is methyl and the compounds wherein R is 2-substituted phenyl, preferably 2-chloro. The 2-chlorophenyl compounds exhibit excellent pre-emergence herbicide activity against grasses with good crops safety for a variety of crops.

Generally, for post-emergent applications, the herbicidal compounds are applied directly to the foliage or other plant parts. For pre-emergence applications, the herbicidal compounds are applied to the growing medium, or prospective growing medium, of the plant. The optimum amount of the herbicidal compound or composition will vary with the particular plant species, and the extent of part plant growth and the particular part of the plant which is contacted. The optimum dosage will also vary with the general location, or environment, of application (e.g., sheltered areas such as greenhouses compared to exposed areas such as fields), and type and degree of control desired. Generally, for both pre- and post-emergent control, the present compounds are applied at rates of about from 0.02 to 60 kg/ha, preferably about from 0.5 to 10 kg/ha.

Also, although in theory the compounds can be applied undiluted, in actual practice they are generally applied as a composition or formulation comprising an effective amount of the compound(s) and an acceptable carrier. An acceptable or compatible carrier (algriculturally acceptable carrier) is one which does not significantly adversely affect the desired biological effect achieved by the active compounds, save to dilute it. Typically, the composition contains about from 0.05 to 95% by weight of the compound of Formula (I) or mixtures thereof. Concentrates can also be made having higher concentrations designed for dilution prior to application. The carrier can be a solid, liquid, or aerosol. The actual compositions can take the form of granules, powders, dusts, solutions, emulsions, slurries, aerosols, and the like.

Suitable solid carriers which can be used include, for example, natural clays (such as kaolin, attapulgite, montmorillonite, etc.), talcs, pyrophyllite, diatomaceous silica, synthetic fine silica, calcium aluminosilicate, tricalcium phosphate, and the like. Also, organic materials, such as, for example, walnut shell flour, cotton-seed hulls, wheat flour, wood flour, wood bark flour, and the like can also be used as carriers. Suitable liquid diluents which can be used include, for example, water, organic solvents (e.g., hydrocarbons such as benzene, toluene, dimethylsulfoxide, kerosene, diesel fuel, fuel oil, petroleum naphtha, etc.), and the like. Suitable aerosol carriers which can be used include conventional aerosol carriers such as halogenated alkanes, etc.

The composition can also contain various promoters and surface-active agents which enhance the rate of transport of the active compound into the plant tissue such as, for example, organic solvents, wetting agents and oils, and in the case of compositions designed for pre-emergence application agents which reduce the leachability of the compound or otherwise enhance soil stability.

The composition can also contain various compatible adjuvants, stabilizers, conditioners, insecticides, fungicides, and if desired, other herbicidally active compounds.

At lower dosages the compounds of formula I also exhibit plant growth regulating activity. These compounds of Formula (I) can be applied in pure form as plant growth regulators, but more pragmatically, as in the case of herbicide applications, are applied in combination with a carrier. The same types of carriers as set forth hereinabove with respect to the herbicide compositions can also be used. Depending on the desired application, the plant growth regulating composition can also contain, or be applied in combination with other compatible ingredients such as desiccants, defoliants, surface-active agents, adjuvants, fungicides, insecticides and compatible selective herbicides. Typically, the plant growth regulating composition will contain a total of about from 0.005 to 90 wt. %, of the compound(s) of Formula (I) depending on whether the composition is intended to be applied directly or diluted first.

A further understanding of the invention can be had in the following non-limiting Preparation and Examples. Wherein, unless expressly stated to the contrary, all temperatures and temperature ranges refer to the Centigrade system and the term "ambient" or "room temperature" refers to about 20°-25° C. The term "percent" or "%" refers to weight percent and the term "mole" or "moles" refers to gram moles. The term "equivalent" refers to a quantity of reagent equal in moles, to the moles of the preceding or succeeding reactant recited in that example in terms of finite moles or finite weight or volume. Where given, proton-magnetic resonance spectrum (p.m.r. or n.m.r.) were determined at 60 mHz, signals are assigned as singlets (s), broad singlets (bs), doublets (d), double doublets (dd), triplets (t), double triplets (dt), quartets (q), and multiplets (m); and cps refers to cycles per second. Also where necessary examples are repeated to provide additional starting material for subsequent examples.

EXAMPLE 1

1,2:5,6-di-O-isopropylidene-3-O-(2-chlorobenzyl)-α-D-glucofuranose

In this example 4.9 grams (0.1 mole) of sodium hydride (50 wt % in mineral oil) was slowly added to an ice-cooled solution of 26 g (0.1 mole) of diacetone D-glucose in 175 ml of tetrahydrofuran under a nitrogen atmosphere. To this mixture was then added 2 g of benzyltriethylammonium chloride followed by the dropwise addition of 16.1 g (0.1 mole) of 2-chlorobenzyl chloride. The mixture was stirred overnight (about 12 hours) at room temperature and then concentrated by evaporation into a viscous mixture. The viscous mixture was dissolved in 200 ml of petroleum ether, and then washed three times with 100 ml of water, dried over anhydrous magnesium sulfate and concentrated by evaporation. The concentrate was heated under reduced pressure to remove unreacted 2-chlorobenzyl chloride affording 37.2 g of the title compound as a liquid.

Similarly by following the same procedure but respectively using the corresponding substituted benzyl chloride or bromide, naphthyl chloride or substituted naphthyl chloride in phace of 2-chlorobenzyl chloride the following compounds can be prepared:

1,2:5,6-di-O-isopropylidene-3-O-(2-methylbenzyl)-α-D-glucofuranose;
1,2:5,6-di-O-isopropylidene-3-O-(naphthylmethyl)-α-D-glucofuranose;
1,2:5,6-di-O-isopropylidene-3-O-(2-methylnaphthylmethyl)-α-D-glucofuranose;
1,2:5,6-di-O-isopropylidene-3-O-(2-chloronapthylmethyl)-α-D-glucofuranose;
1,2:5,6-di-O-isopropylidene-3-O-(2-bromobenzyl)-α-D-glucofuranose;
1,2:5,6-di-O-isopropylidene-3-O-(2-fluorobenzyl)-α-D-glucofuranose;
1,2:5,6-di-O-isopropylidene-3-O-(2-iodobenzyl)-α-D-glucofuranose;
1,2:5,6-di-O-isopropylidene-3-O-(4-chlorobenzyl)-α-D-glucofuranose;
1,2:5,6-di-O-isopropylidene-3-O-(3-chlorobenzyl)-α-D-glucofuranose;
1,2:5,6-di-O-isopropylidene-3-O-(4-methylphenyl)-α-D-glucofuranose;
1,2:5,6-di-O-isopropylidene-3-O-(2,3,4-trichlorobenzyl)-α-D-glucofuranose;
1,2:5,6-di-O-isopropylidene-3-O-(2-chloro-3,4-dimethylbenzyl)-α-D-glucofuranose;
1,2:5,6-di-O-isopropylidene-3-O-(2-methyl-4-bromobenzyl)-α-D-glucofuranose;
1,2:5,6-di-O-isopropylidene-3-O-(2-chloro-4-trifluoromethylbenzyl)-α-D-glucofuranose;
1,2:5,6-di-O-isopropylidene-3-O-(2-chloro-3-bromobenzyl)-α-D-glucofuranose;
1,2:5,6-di-O-isopropylidene-3-O-(2-butyl-3-fluorobenzyl)-α-D-glucofuranose;
1,2:5,6-di-O-isopropylidene-3-O-(3,4-dichlorobenzyl)-α-D-glucofuranose;
1,2:5,6-di-O-isopropylidene-3-O-(3-ethyl-4-bromobenzyl)-α-D-glucofuranose;
1,2:5,6-di-O-isopropylidene-3-O-(3-butyl-4-butylbenzyl)-α-D-glucofuranose;

EXAMPLE 2

1,2-O-isopropylidene-3-O-(2-chlorobenzyl)-α-D-glucofuranose

In this example a mixture containing 167.9 g of 1,2:5,6-di-O-isopropylidene-3-O-(2-chlorobenzyl)-α-D-glucofuranose in 495 ml of glacial acetic acid and 275 ml of water was stirred overnight (about 12 hours) at 40° C. The mixture was then cooled to room temperature and the acetic acid was then carefully neutralized by the stepwise addition of saturated aqueous potassium carbonate solution. The neutralized solution was then extracted with three 500 ml portions of methylene chloride, washed twice with 500 ml of water, then with saturated aqueous sodium chloride. The washed solution was then dried over anhydrous magnesium sulfate and evaporated under vacuum affording 129.5 g of the title compound as a syrup.

Similarly, the 5,6-O-isopropylidene group can be cleaved from the products listed in Example 1 by following the same procedure.

EXAMPLE 3

1,2-O-isopropylidene-3-O-(2-chlorobenzyl)-α-D-xylo-pentodialdo-1,4-furanose

In this example a solution of 24.3 g (0.11 mole) of sodium metaperiodate in about 275 ml of water was added dropwise to a solution containing 34 g of 1,2-O-isopropylidene-3-O-(2-chlorobenzyl)-α-D-glucofuranose in about 275 ml of absolute methanol cooled in an ice-water bath. The mixture was stirred at 0° C. for 90 minutes and then 3 ml of ethylene glycol was added and the mixture stirred for about another 15 minutes. The methanol was then evaporated off and the remaining aqueous phase was extracted three times with 200 ml of methylene chloride. The combined organic extracts were washed with water, dried over magnesium sulfate and evaporated under vacuum affording 29.8 g of the title compound as a syrup.

Similarly by following the same procedure the other products indicated in the last paragraph of Example 2 can be converted to the corresponding dialdo products.

EXAMPLE 4

1,2-O-isopropylidene-3-O-(2-chlorobenzyl)-6,7-dideoxy-α-D-gluco-heptofuranose and β-L-ido-heptofuranose In this example a solution of ethyl magnesium bromide was prepared by the dropwise addition of 25.4 ml of ethyl bromide to 6.6 g of magnesium turnings in 170 ml of anhydrous ethyl ether. A solution containing 11.2 g of 1,2-O-isopropylidene-3-O-(2-chlorobenzyl)-α-D-xylo-pentodialdo-1,4-furanose in 120 ml of ethyl ether was then slowly added to the resulting mixture and the solution was refluxed for 90 minutes. The mixture was cooled and then added to 120 ml of aqueous 25 wt % ammonium chloride cooled in an ice-water bath. 200 ml of ethyl ether was added. The ethyl ether phase was separated and washed with 85 ml of 25 wt % aqueous ammonium chloride, dried over anhydrous magnesium sulfate and evaporated to a syrup consisting of the D-gluco and L-ido isomers. The syrup subsequently crystallized and the crystallized product was slurried with hexane and then filtered affording 4.9 g of the title L-ido compound as a white powder; m.p. 90°–93° C.

Similarly, by applying the above procedure to the products indicated in the last paragraph of Example 3 hereinabove the following compounds can be made:

1,2-O-isopropylidene-3-O-(2-methylbenzyl)-6,7-dideoxy-α-D-gluco-heptofuranose and β-L-ido-heptofuranose;

1,2-O-isopropylidene-3-O-(naphthylmethyl)-6,7-dideoxy-α-D-gluco-heptofuranose and β-L-ido-heptofuranose;

1,2-O-isopropylidene-3-O-(2-methylnaphthylmethyl)-6,7-dideoxy-α-D-gluco-heptofuranose and β-L-ido-heptofuranose;

1,2-O-isopropylidene-3-O-(2-chloronaphthylmethyl)6,7-dideoxy-α-D-gluco-heptofuranose and β-L-ido-heptofuranose;

1,2-O-isopropylidene-3-O-(2-bromobenzyl)-6,7-dideoxy-α-D-gluco-heptofuranose and β-L-ido-heptofuranose;

1,2-O-isopropylidene-3-O-(2-fluorobenzyl)-6,7-dideoxy-α-D-gluco-heptofuranose and β-L-ido-heptofuranose;

1,2-O-isopropylidene-3-O-(2-iodobenzyl)-6,7-dideoxy-α-D-gluco-heptofuranose and β-L-ido-heptofuranose;

1,2-O-isopropylidene-3-O-(4-chlorobenzyl)-6,7-dideoxy-α-D-gluco-heptofuranose and β-L-ido-heptofuranose;

1,2-O-isopropylidene-3-O-(3-chlorobenzyl)-6,7-dideoxy-α-D-gluco-heptofuranose and β-L-ido-heptofuranose;

1,2-O-isopropylidene-3-O-(4-methylbenzyl)-6,7-dideoxy-α-D-gluco-heptofuranose and β-L-ido-heptofuranose;

1,2-O-isopropylidene-3-O-(2,3,4-trichlorobenzyl)-6,7-dideoxy-α-D-gluco-heptofuranose and β-L-ido-heptofuranose;

1,2-O-isopropylidene-3-O-(2-chloro-3,4-dimethylbenzyl)-6,7-dideoxy-α-D-gluco-heptofuranose and β-L-ido-heptofuranose;

1,2-O-isopropylidene-3-O-(2-methyl-4-bromobenzyl)-6,7-dideoxy-α-D-gluco-heptofuranose and β-L-ido-heptofuranose;

1,2-O-isopropylidene-3-O-(2-chloro-4-trifluoromethylbenzyl)-6,7-dideoxy-α-D-gluco-heptofuranose and β-L-ido-heptofuranose;

1,2-O-isopropylidene-3-O-(2-chloro-3-bromobenzyl)6,7-dideoxy-α-D-gluco-heptofuranose and β-L-ido-heptofuranose;

1,2-O-isopropylidene-3-O-(2-butyl-3-fluorobenzyl)6,7-dideoxy-α-D-gluco-heptofuranose and β-L-ido-heptofuranose;

1,2-O-isopropylidene-3-O-(3,4-dichlorobenzyl)-6,7-dideoxy-α-D-gluco-heptofuranose and β-L-ido-heptofuranose;

1,2-O-isopropylidene-3-O-(3-ethyl-4-bromobenzyl)-6,7-dideoxy-α-D-gluco-heptofuranose and β-L-ido-heptofuranose;

and 1,2-O-isopropylidene-3-O-(3-butyl-4-butylbenzyl)-6,7-dideoxy-α-D-gluco-heptofuranose and β-L-ido-heptofuranose.

Similarly, by applying this procedure to the corresponding pentodialdo-1,4-furanose using methyl iodide in place of ethyl bromide the following compounds can be prepared:

1,2-O-isopropylidene-3-O-(2-chlorobenzyl)-6-deoxy-α-D-glucofuranose and β-L-idofuranose;

1,2-O-isopropylidene-3-O-(2-methylbenzyl)-6-deoxy-α-D-glucofuranose and β-L-idofuranose;

1,2-O-isopropylidene-3-O-(naphthylmethyl)-6-deoxy-α-D-glucofuranose and β-L-idofuranose;

1,2-O-isopropylidene-3-O-(2-methylnaphthylmethyl)-6-deoxy-α-D-glucofuranose and β-L-idofuranose;

1,2-O-isopropylidene-3-O-(2-chloronaphthylmethyl)-6-deoxy-α-D-glucofuranose and β-L-idofuranose;

1,2-O-isopropylidene-3-O-(2-bromobenzyl)-6-deoxy-α-D-glucofuranose and β-L-idofuranose;

1,2-O-isopropylidene-3-O-(2-fluorobenzyl)-6-deoxy-α-D-glucofuranose and β-L-idofuranose;

1,2-O-isopropylidene-3-O-(2-iodobenzyl)-6-deoxy-α-D-glucofuranose and β-L-idofuranose;

1,2-O-isopropylidene-3-O-(4-chlorobenzyl)-6-deoxy-α-D-glucofuranose and β-L-idofuranose;

1,2-O-isopropylidene-3-O-(3-chlorobenzyl)-6-deoxy-α-D-glucofuranose and β-L-idofuranose;
1,2-O-isopropylidene-3-O-(4-methylbenzyl)-6-deoxy-α-D-glucofuranose and β-L-idofuranose;
1,2-O-isopropylidene-3-O-(2,3,4-trichlorobenzyl)-6-deoxy-α-D-glucofuranose and β-L-idofuranose;
1,2-O-isopropylidene-3-O-(2-chloro-3,4-dimethylbenzyl)-6-deoxy-α-D-glucofuranose and β-L-idofuranose;
1,2-O-isopropylidene-3-O-(2-methyl-4-bromobenzyl)-6-deoxy-α-D-glucofuranose and β-L-idofuranose;
1,2-O-isopropylidene-3-O-(2-chloro-4-trifluoromethylbenzyl)-6-deoxy-α-D-glucofuranose and β-L-idofuranose;
1,2-O-isopropylidene-3-O-(2-chloro-3-bromobenzyl)-6-deoxy-α-D-glucofuranose and β-L-idofuranose;
1,2-O-isopropylidene-3-O-(2-butyl-3-fluorobenzyl)-6-deoxy-α-D-glucofuranose and β-L-idofuranose;
1,2-O-isopropylidene-3-O-(3,4-dichlorobenzyl)-6-deoxy-α-D-glucofuranose and β-L-idofuranose;
1,2-O-isopropylidene-3-O-(3-ethyl-4-bromobenzyl)-6-deoxy-α-D-glucofuranose and β-L-idofuranose; and
1,2-O-isopropylidene-3-O-(3-butyl-4-butylbenzyl)-6-deoxy-α-D-glucofuranose and β-L-idofuranose.

Similarly, by following this procedure, using propyl bromide in place of ethyl bromide the following compounds can be prepared:
1,2-O-isopropylidene-3-O-(2-chlorobenzyl)-6,7,8-trideoxy-α-D-gluco-octofuranose and β-L-ido-octofuranose;
1,2-O-isopropylidene-3-O-(2-methylbenzyl)-6,7,8-trideoxy-α-D-gluco-octofuranose and β-L-ido-octofuranose;
1,2-O-isopropylidene-3-O-(naphthylmethyl)-6,7,8-trideoxy-α-D-gluco-octofuranose and β-L-ido-octofuranose;
1,2-O-isopropylidene-3-O-(2-methylnaphthylmethyl)6,7,8-trideoxy-α-D-gluco-octofuranose and β-L-ido-octofuranose;
1,2-O-isopropylidene-3-O-(2-chloronaphthylmethyl)6,7,8-trideoxy-α-D-gluco-octofuranose and β-L-ido-octofuranose;
1,2-O-isopropylidene-3-O-(2-bromobenzyl)-6,7,8-trideoxy-α-D-gluco-octofuranose and β-L-ido-octofuranose;
1,2-O-isopropylidene-3-O-(2-fluorobenzyl)-6,7,8-trideoxy-α-D-gluco-octofuranose and β-L-ido-octofuranose;
1,2-O-isopropylidene-3-O-(2-iodobenzyl)-6,7,8-trideoxy-α-D-gluco-octofuranose and β-L-ido-octofuranose;
1,2-O-isopropylidene-3-O-(4-chlorobenzyl)-6,7,8-trideoxy-α-D-gluco-octofuranose and β-L-ido-octofuranose;
1,2-O-isopropylidene-3-O-(3-chlorobenzyl)-6,7,8-trideoxy-α-D-gluco-octofuranose and β-L-ido-octofuranose;
1,2-O-isopropylidene-3-O-(4-methylbenzyl)-6,7,8-trideoxy-α-D-gluco-octofuranose and β-L-ido-octofuranose;
1,2-O-isopropylidene-3-O-(2,3,4-trichlorobenzyl)6,7,8-trideoxy-α-D-gluco-octofuranose and β-L-ido-octofuranose;
1,2-O-isopropylidene-3-O-(2-chloro-3,4-dimethylbenzyl)-6,7,8-trideoxy-α-D-gluco-octofuranose and β-L-ido-octofuranose;
1,2O-isopropylidene-3-O-(2-methyl-4-bromobenzyl)6,7,8-trideoxy-α-D-gluco-octofuranose and β-L-ido-octofuranose;
1,2-O-isopropylidene-3-O-(2-chloro-4-trifluoromethylbenzyl)-6,7,8-trideoxy-α-D-gluco-octofuranose and β-L-ido-octofuranose;
1,2-O-isopropylidene-3-O-(2-chloro-3-bromobenzyl)6,7,8-trideoxy-α-D-gluco-octofuranose and β-L-ido-octofuranose;
1,2-O-isopropylidene-3-O-(2-butyl-3-fluorobenzyl)6,7,8-trideoxy-α-D-gluco-octofuranose and β-L-ido-octofuranose;
1,2-O-isopropylidene-3-O-(3,4-dichlorobenzyl)-6,7,8-trideoxy-α-D-gluco-octofuranose and β-L-ido-octofuranose;
1,2-O-isopropylidene-3-O-(3-ethyl-4-bromobenzyl)6,7,8-trideoxy-α-D-gluco-octofuranose and β-L-ido-octofuranose; and
1,2-O-isopropylidene-3-O-(3-butyl-4-butylbenzyl)6,7,8-trideoxy-α-D-gluco-octofuranose and β-L-ido-octofuranose.

Similarly by using butyl chloride in place of ethyl bromide the following compounds can be prepared:
1,2-O-isopropylidene-3-O-(2-chlorobenzyl)-5-C-butyl-α-D-gluco-pentofuranose and β-L-ido-pentofuranose;
1,2-O-isopropylidene-3-O-(2-methylbenzyl)-5-C-butyl-α-D-gluco-pentofuranose and β-L-ido-pentofuranose;
1,2-O-isopropylidene-3-O-(naphthylmethyl)-5-C-butyl-α-D-gluco-pentofuranose and β-L-ido-pentofuranose;
1,2-O0isopropylidene-3-O-(2-methylnaphthylmethyl)-5-C-butyl-α-D-gluco-pentofuranose and β-L-ido-pentofuranose;
1,2-O-isopropylidene-3-O-(2-chloronaphthylmethyl)-5-C-butyl-α-D-gluco-pentofuranose and β-L-ido-pentofuranose;
1,2-O-isopropylidene-3-O-(2-bromobenzyl)-5-C-butyl-α-D-gluco-pentofuranose and β-L-ido-pentofuranose;
1,2-O-isopropylidene-3-O-(2-fluorobenzyl)-5-C-butyl-α-D-gluco-pentofuranose and β-L-ido-pentofuranose;
1,2-O-isopropylidene-3-O-(2-iodobenzyl)-5-C-butyl-α-D-gluco-pentofuranose and β-L-ido-pentofuranose;
1,2-O-isopropylidene-3-O-(4-chlorobenzyl)-5-C-butyl-α-D-gluco-pentofuranose and β-L-ido-pentofuranose;
1,2-O-isopropylidene-3-O-(3-chlorobenzyl)-5-C-butyl-α-D-gluco-pentofuranose and β-L-ido-pentofuranose;
1,2-O-isopropylidene-3-O-(4-methylbenzyl)-5-C-butyl-α-D-gluco-pentofuranose and β-L-ido-pentofuranose;
1,2-O-isopropylidene-3-O-(2,3,4-trichlorobenzyl)-5-C-butyl-α-D-gluco-pentofuranose and β-L-ido-pentofuranose;
1,2-O-isopropylidene-3-O-(2-chloro-3,4-dimethylbenzyl)-5-C-butyl-α-D-gluco-pentofuranose and β-L-ido-pentofuranose;
1,2-O-isopropylidene-3-O-(2-methyl-4-bromobenzyl)-5-C-butyl-α-D-gluco-pentofuranose and β-L-ido-pentofuranose;
1,2-O-isopropylidene-3-O-(2-chloro-4-trifluoromethylbenzyl)-5-C-butyl-α-D-gluco-pentofuranose and β-L-ido-pentofuranose;

1,2-O-isopropylidene-3-O-(2-chloro-3-bromobenzyl)-5-C-butyl-α-D-gluco-pentofuranose and β-L-ido-pentofuranose;

1,2-O-isopropylidene-3-O-(2-butyl-3-fluorobenzyl)-5-C-butyl-α-D-gluco-pentofuranose and β-L-ido-pentofuranose;

1,2-O-isopropylidene-3-O-(3,4-dichlorobenzyl)-5-C-butyl-α-D-gluco-pentofuranose and β-L-ido-pentofuranose;

1,2-O-isopropylidene-3-O-(3-ethyl-4-bromobenzyl)-5-C-butyl-α-D-gluco-pentofuranose and β-L-ido-pentofuranose;
and 1,2-O-isopropylidene-3-O-(3-butyl-4-butylbenzyl)-5-C-butyl-α-D-gluco-pentofuranose and β-L-ido-pentofuranose.

EXAMPLE 5

1,2-O-isopropylidene-3-O-(2-chlorobenzyl)-6,7-dideoxy-α-D-xylo-heptofuranos-5-ulose In this example Jones reagent (i.e. $H_2CrO_4$) was prepared by dissolving 26.72 g of chromium trioxide ($CrO_3$) in sufficient water to yield a volume of 77 ml and stirring in 23 ml of concentrated sulfuric acid to yield a total volume of 100 ml. 12 ml of this solution was then added dropwise to a solution containing 3.4 g (0.01 mole) of 1,2-O-isopropylidene-3-O-(2-chlorobenzyl)-6,7-dideoxy-α-D-gluco-heptofuranose and the 5-epimer in 125 ml of acetone at −60° C. The mixture was allowed to warm to −5°–0° C. over a 1 hour period and then stirred at about 0° C. for about five hours. The mixture was then diluted with 500 ml of ethyl ether, washed three times with 200 ml of water. The water washes were respectively extracted with 200 ml of ethyl ether. The ethyl ether extracts were combined, dried over magnesium sulfate, and evaporated under vacuum affording 3.4 g of the title compound as a yellow syrup which was subsequently further purified by high pressure liquid chromatography eluting with ethyl acetate:-hexane (1:4 by volume).

Similarly, by respectively applying the above procedure to the products listed in Example 4 hereinabove, the following compounds can be prepared:

1,2-O-isopropylidene-3-O-(2-methylbenzyl)-6,7-dideoxy-α-D-xylo-heptofuranos-5-ulose;

1,2-O-isopropylidene-3-O-(naphthylmethyl)-6,7-dideoxy-α-D-xylo-heptofuranos-5-ulose;

1,2-O-isopropylidene-3-O-(2-methylnaphthylmethyl)-6,7-dideoxy-α-D-xylo-heptofuranos-5-ulose;

1,2-O-isopropylidene-3-O-(2-chloronaphthylmethyl)-6,7-dideoxy-α-D-xylo-heptofuranos-5-ulose;

1,2-O-isopropylidene-3-O-(2-bromobenzyl)-6,7-dideoxy-α-D-xylo-heptofuranos-5-ulose;

1,2-O-isopropylidene-3-O-(2-fluorobenzyl)-6,7-dideoxy-α-D-xylo-heptofuranos-5-ulose;

1,2-O-isopropylidene-3-O-(2-iodobenzyl)-6,7-dideoxy-α-D-xylo-heptofuranos-5-ulose;

1,2-O-isopropylidene-3-O-(4-chlorobenzyl)-6,7-dideoxy-α-D-xylo-heptofuranos-5-ulose;

1,2-O-isopropylidene-3-O-(3-chlorobenzyl)-6,7-dideoxy-α-D-xylo-heptofuranos-5-ulose;

1,2-O-isopropylidene-3-O-(4-methylbenzyl)-6,7-dideoxy-α-D-xylo-heptofuranos-5-ulose;

1,2-O-isopropylidene-3-O-(2,3,4-trichlorobenzyl)-6,7-dideoxy-α-D-xylo-heptofuranos-5-ulose;

1,2-O-isopropylidene-3-O-(2-chloro-3,4-dimethylbenzyl)-6,7-dideoxy-α-D-xylo-heptofuranos-5-ulose;

1,2-O-isopropylidene-3-O-(2-methoxy-4-bromobenzyl)-6,7-dideoxy-α-D-xylo-heptofuranos-5-ulose;

1,2-O-isopropylidene-3-O-(2-chloro-4-trifluoromethylbenzyl)-6,7-dideoxy-α-D-xylo-heptofuranos-5-ulose;

1,2-O-isopropylidene-3-O-(2-chloro-3-bromobenzyl)-6,7-dideoxy-α-D-xylo-heptofuranos-5-ulose;

1,2-O-isopropylidene-3-O-(2-butyl-3-fluorobenzyl)-6,7-dideoxy-α-D-xylo-heptofuranos-5-ulose;

1,2-O-isopropylidene-3-O-(3,4-dichlorobenzyl)-6,7-dideoxy-α-D-xylo-heptofuranos-5-ulose;

1,2-O-isopropylidene-3-O-(3-ethoxy-4-bromobenzyl)-6,7-dideoxy-α-D-xylo-heptofuranos-5-ulose;

1,2-O-isopropylidene-3-O-(3-butyl-4-butylbenzyl)-6,7-dideoxy-α-D-xylo-heptofuranos-5-ulose;

1,2-O-isopropylidene-3-O-(2-chlorobenzyl)-6-deoxy-α-D-xylo-hexofuranos-5-ulose;

1,2-O-isopropylidene-3-O-(2-methylbenzyl)-6-deoxy-α-D-xylo-hexofuranos-5-ulose;

1,2-O-isopropylidene-3-O-(naphthylmethyl)-6-deoxy-α-D-xylo-hexofuranos-5-ulose;

1,2-O-isopropylidene-3-O-(2-methylnaphthylmethyl)-6-deoxy-α-D-xylo-hexofuranos-5-ulose;

1,2-O-isopropylidene-3-O-(2-chloronaphthylmethyl)-6-deoxy-α-D-xylo-hexofuranos-5-ulose;

1,2-O-isopropylidene-3-O-(2-bromobenzyl)-6-deoxy-α-D-xylo-hexofuranos-5-ulose;

1,2-O-isopropylidene-3-O-(2-fluorobenzyl)-6-deoxy-α-D-xylo-hexofuranos-5-ulose;

1,2-O-isopropylidene-3-O-(2-iodobenzyl)-6-deoxy-α-D-xylo-hexofuranos-5-ulose;

1,2-O-isopropylidene-3-O-(4-chlorobenzyl)-6-deoxy-α-D-xylo-hexofuranos-5-ulose;

1,2-O-isopropylidene-3-O-(3-chlorobenzyl)-6-deoxy-α-D-xylo-hexofuranos-5-ulose;

1,2-O-isopropylidene-3-O-(4-methylbenzyl)-6-deoxy-α-D-xylo-hexofuranos-5-ulose;

1,2-O-isopropylidene-3-O-(2,3,4-trichlorobenzyl)-6-deoxy-α-D-xylo-hexofuranos-5-ulose;

1,2-O-isopropylidene-3-O-(2-chloro-3,4-dimethylbenzyl)-6-deoxy-α-D-xylo-hexofuranos-5-ulose;

1,2-O-isopropylidene-3-O-(2-methoxy-4-bromobenzyl)-6-deoxy-α-D-xylo-hexofuranos-5-ulose;

1,2-O-isopropylidene-3-O-(2-chloro-4-trifluoromethylbenzyl)-6-deoxy-α-D-xylo-hexofuranos-5-ulose;

1,2-O-isopropylidene-3-O-(2-chloro-3-bromobenzyl)-6-deoxy-α-D-xylo-hexofuranos-5-ulose;

1,2-O-isopropylidene-3-O-(2-butyl-3-fluorobenzyl)-6-deoxy-α-D-xylo-hexofuranos-5-ulose;

1,2-O-isopropylidene-3-O-(3,4-dichlorobenzyl)-6-deoxy-α-D-xylo-hexofuranos-5-ulose;

1,2-O-isopropylidene-3-O-(3-ethyl-4-bromobenzyl)-6-deoxy-α-D-xylo-hexofuranos-5-ulose;

1,2-O-isopropylidene-3-O-(3-butyl-4-butylbenzyl)-6-deoxy-α-D-xylo-hexofuranos-5-ulose;

1,2-O-isopropylidene-3-O-(2-chlorobenzyl)-6,7,8-trideoxy-α-D-xylo-octofuranos-5-ulose;

1,2-O-isopropylidene-3-O-(2-methylbenzyl)-6,7,8-trideoxy-α-D-xylo-octofuranos-5-ulose;

1,2-O-isopropylidene-3-O-(naphthylmethyl)-6,7,8-trideoxy-α-D-xylo-octofuranos-5-ulose;

1,2-O-isopropylidene-3-O-(2-methylnaphthylmethyl)-6,7,8-trideoxy-α-D-xylo-octofuranos-5-ulose;

1,2-O-isopropylidene-3-O-(2-chloronaphthylmethyl)-6,7,8-trideoxy-α-D-xylo-octofuranos-5-ulose;

1,2-O-isopropylidene-3-O-(2-bromobenzyl)-6,7,8-trideoxy-α-D-xylo-octofuranos-5-ulose;

1,2-O-isopropylidene-3-O-(2-fluorobenzyl)-6,7,8-trideoxy-α-D-xylo-octofuranos-5-ulose;

1,2-O-isopropylidene-3-O-(2-iodobenzyl)-6,7,8-
trideoxy-α-D-xylo-octofuranos-5-ulose;
1,2-O-isopropylidene-3-O-(4-chlorobenzyl)-6,7,8-
trideoxy-α-D-xylo-octofuranos-5-ulose;
1,2-O-isopropylidene-3-O-(3-chlorobenzyl)-6,7,8-
trideoxy-α-D-xylo-octofuranos-5-ulose;
1,2-O-isopropylidene-3-O-(4-methylbenzyl)-6,7,8-
trideoxy-α-D-xylo-octofuranos-5-ulose;
1,2-O-isopropylidene-3-O-(2,3,4-trichlorobenzyl)-6,7,8-
trideoxy-α-D-xylo-octofuranos-5-ulose;
1,2-O-isopropylidene-3-O-(2-chloro-3,4-dimethylbenzyl)-6,7,8-trideoxy-α-D-xylo-octofuranos-5-ulose;
1,2-O-isopropylidene-3-O-(2-methyl-4-bromobenzyl)-
6,7,8-trideoxy-α-D-xylo-octofuranos-5-ulose;
1,2-O-isopropylidene-3-O-(2-chloro-4-trifluoromethylbenzyl)-6,7,8-trideoxy-α-D-xylo-octofuranos-5-ulose;
1,2-O-isopropylidene-3-O-(2-chloro-3-bromobenzyl)-
6,7,8-trideoxy-α-D-xylo-octofuranos-5-ulose;
1,2-O-isopropylidene-3-O-(2-butyl-3-fluorobenzyl)-
6,7,8-trideoxy-α-D-xylo-octofuranos-5-ulose;
1,2-O-isopropylidene-3-O-(3,4-dichlorobenzyl)-6,7,8-
trideoxy-α-D-xylo-octofuranos-5-ulose;
1,2-O-isopropylidene-3-O-(3-ethyl-4-bromobenzyl)-
6,7,8-trideoxy-α-D-xylo-octofuranos-5-ulose;
1,2-O-isopropylidene-3-O-(3-butyl-4-butylbenzyl)-6,7,8-
trideoxy-α-D-xylo-octofuranos-5-ulose;
1,2-O-isopropylidene-3-O-(2-chlorobenzyl)-5-C-butyl-
α-D-xylo-pentodialdofuranose;
1,2-O-isopropylidene-3-O-(2-methylbenzyl)-5-C-butyl-
α-D-xylo-pentodialdofuranose;
1,2-O-isopropylidene-3-O-(naphthylmethyl)-5-C-butyl-
α-D-xylo-pentodialdofuranose;
1,2-O-isopropylidene-3-O-(2-methylnaphthylmethyl)-5-
C-butyl-α-D-xylo-pentodialdofuranose;
1,2-O-isopropylidene-3-O-(2-chloronaphthylmethyl)-5-
C-butyl-α-D-xylo-pentodialdofuranose;
1,2-O-isopropylidene-3-O-(2-bromobenzyl)-5-C-butyl-
α-D-xylo-pentodialdofuranose;
1,2-O-isopropylidene-3-O-(2-fluorobenzyl)-5-C-butyl-
α-D-xylo-pentodialdofuranose;
1,2-O-isopropylidene-3-O-(2-iodobenzyl)-5-C-butyl-α-
D-xylo-pentodialdofuranose;
1,2-O-isopropylidene-3-O-(4-chlorobenzyl)-5-C-butyl-
α-D-xylo-pentodialdofuranose;
1,2-O-isopropylidene-3-O-(3-chlorobenzyl)-5-C-butyl-
α-D-xylo-pentodialdofuranose;
1,2-O-isopropylidene-3-O-(4-methylbenzyl)-5-C-butyl-
α-D-xylo-pentodialdofuranose;
1,2-O-isopropylidene-3-O-(2,3,4-trichlorobenzyl)-5-C-
butyl-α-D-xylo-pentodialdofuranose;
1,2-O-isopropylidene-3-O-(2-chloro-3,4-dimethylbenzyl)-5-C-butyl-α-D-xylo-pentodialdofuranose;
1,2-O-isopropylidene-3-O-(2-methyl-4-bromobenzyl)-5-
C-butyl-α-D-xylo-pentodialdofuranose;
1,2-O-isopropylidene-3-O-(2-chloro-4-trifluoromethylbenzyl)-5-C-butyl-α-D-xylo-pentodialdofuranose;
1,2-O-isopropylidene-3-O-(2-chloro-3-bromobenzyl)-5-
C-butyl-α-D-xylo-pentodialdofuranose;
1,2-O-isopropylidene-3-O-(2-butyl-3-fluorobenzyl)-5-C-
butyl-α-D-xylo-pentodialdofuranose;
1,2-O-isopropylidene-3-O-(3,4-dichlorobenzyl)-5-C-
butyl-α-D-xylo-pentodialdofuranose;
1,2-O-isopropylidene-3-O-(3-ethyl-4-bromobenzyl)-5-
C-butyl-α-D-xylo-pentodialdofuranose; and
1,2-O-isopropylidene-3-O-(3-butyl-4-butylbenzyl)-5-C-
butyl-α-D-xylo-pentodialdofuranose.

EXAMPLE 6

3-O-(2-chlorobenzyl)-6,7-dideoxy-α-D-xylo-heptofuranos-5-ulose

In this example a solution containing 6.8 g (0.02 mole) of 1,2-O-isopropylidene-3-O-(2-chlorobenzyl)-6,7-dideoxy-α-D-xylo-heptofuranos-5-ulose in 60 ml of aqueous trifluoroacetic acid (9 parts by volume acid per part water) was stirred at room temperature for 3 hours and then concentrated by evaporation at 50°–60° C. affording a residue which crystallized upon standing. The crystallized residue was washed with hexane and filtered affording the title compound as a solid; m.p. 130°–133° C.

Similarly, by following the same procedure the isopropylidene ether group can be cleaved from the products listed or indicated in Example 5 and 5A hereinabove.

EXAMPLE 7

1,2-O-(2-methylpropylidene)-3-O-(2-chlorobenzyl)-6,7-dideoxy-α-D-xylo-heptofuranos-5-ulose (formula I $R^2$=H, $R^3$=isopropyl)

In this example 3.5 g of isobutyraldehyde was added to a mixture containing 3.0 g of 3-O-(2-chlorobenzyl)-6,7-dideoxy-α-D-xylo-heptofuranos-5-ulose; 4 g of anhydrous copper sulfate and a catalytic amount (about 50–200 mg) of p-toluenesulfonic acid monohydrate in 50 ml of toluene at room temperature. The mixture was stirred for 1 hour at 50° C. and then for 3 hours at room temperature. The mixture was then diluted with 50 ml of toluene and washed with saturated sodium bicarbonate solution, twice with 50 ml of water and then with 50 ml of saturated aqueous sodium chloride solution, dried over anhydrous magnesium sulfate, and concentrated by evaporation. The concentrate was then subjected to flash column chromatography, eluting with 1:4 vols. of tetrahydrofuran:hexane mixtures, affording 2.9 g of the title compound.

Similarly, by following the procedure of Example 6 and the above procedure the corresponding 1,2-O-(2-methylpropylidene) homolog of the compounds listed or indicated in Example 5 can be prepared, for example:
1,2-O-(2-methylpropylidene)-3-O-(2-methylbenzyl)-6,7-dideoxy-α-D-xylo-heptofuranos-5-ulose;
1,2-O-(2-methylpropylidene)-3-O-(2-chlorobenzyl)-6-deoxy-α-D-xylo-hexofuranos-5-ulose;
1,2-O-(2-methylpropylidene)-3-O-(2-chlorobenzyl)-6,7,8-trideoxy-α-D-xylo-octofuranos-5-ulose;
1,2-O-(2-methylpropylidene)-3-O-(2-chlorobenzyl)-5-C-butyl-α-D-xylo-pentodialdofuranose; etc.

Similarly, by following the procedure of Example 6 and the above procedure but using paraformaldehyde in place of isobutyraldehyde, the corresponding 1,2-methylene homologs of the compounds of Examples 5 and 5A can be prepared for example:
1,2-O-methylene-3-O-(2-chlorobenzyl)-6,7-dideoxy-α-D-xylo-heptofuranos-5-ulose;
1,2-O-methylene-3-O-(2-chlorobenzyl)-6-deoxy-α-D-xylo-hexofuranos-5-ulose;
1,2-O-methylene-3-O-(2-chlorobenzyl)-6,7,8-trideoxy-α-D-xylo-octofuranos-5-ulose;
1,2-O-methylene-3-O-(2-chlorobenzyl)-5-C-butyl-α-D-xylo-pentodialdofuranose; etc.

Similarly, by following the procedure of the above procedure but respectively using propionaldehyde diethyl acetal; chloroacetaldehyde; 3-pentanone; 2-butanone; 2-pentanone; 6-bromo-3-hexanone; 4-fluoro-2-pentanone and cyclohexanone the corresponding 1,2-O-propylidene; 1,2-O-(2-chloroethylidene); 1,2-O-(1-ethylpropylidene); 1,2-O-(1-methylpropylidene); 1,2-O-(1-methylbutylidene); 1,2-O-(1-ethyl-4-bromobutylidene); 1,2-O-(1-methyl-3-fluorobutylidene); and 1,2-O-cyclohexylidene analogs of the products listed in Example 5 can be respectively prepared.

EXAMPLE 8

1,2-O-isopropylidene-3-O-(2-chlorobenzyl)-5-C-methyl-6-deoxy-α-D-glucofuranose and β-L-idofuranose In this example a solution containing 15 g of 1,2-O-isopropylidene-3-O-(2-chlorobenzyl)-6-deoxy-α-D-xylo-hexofuranos-5-ulose in 400 ml of ethyl ether was added dropwise to a stirred solution of 150 ml of 2.8 molar solution of methylmagnesium bromide in ethyl ether at about −20° C. The temperature of the resulting mixture was allowed to rise to room temperature (about 20°–25° C.) and was then stirred for about 1½ hours. The mixture was then poured into an aqueous 25 wt.% ammonium chloride solution at about 0° C. and then extracted three times with 200 ml of ethyl ether. The extracts were combined and then washed twice with 100 ml of water, dried over magnesium sulfate, filtered, and evaporated affording the title compound.

Similarly, the corresponding 5-methyl homologs of the products listed or indicated in Examples 5 and 8 hereinabove can be prepared by applying the above-described procedure to these compounds.

EXAMPLE 9

1,2-O-isopropylidene-3-O-(2-chlorobenzyl)-5-O-chloroacetyl-6,7-dideoxy-α-D-gluco-heptofuranose and β-L-ido-heptofuranose In this example 1.1 g (0.01 mole) of chloroacetyl chloride was added dropwise to an ice cooled stirred solution containing 3.1 g (0.01 mole) of 1,2-O-isopropylidene-3-O-(2-chlorobenzyl)-6,7-dideoxy-α-D-gluco-heptofuranose and β-L-ido-heptofuranose and 0.95 g of pyridine in 50 ml of ethyl acetate. The temperature of the mixture was allowed to raise to room temperature (about 20°–25° C.) and was stirred overnight (about 15 hours) at room temperature. The mixture was then washed several times with water. The ethyl acetate layer was separated off, and then dried over magnesium sulfate and evaporated to dryness. The residue was dissolved in 100 ml of ethyl ether, then washed with water and evaporated under vacuum affording the title compound.

Similarly, by applying the above procedure to the products of Examples 4 and 8, the corresponding chloroacetyl analogs thereof can be prepared, for example:

1,2-O-isopropylidene-3-O-(2-methylbenzyl)-5-O-chloro-acetyl-6,7-dideoxy-α-D-gluco-heptofuranose and β-L-ido-heptofuranose;

1,2-O-isopropylidene-3-O-(naphthylmethyl)-5-O-chloroacetyl-6,7-dideoxy-α-D-gluco-heptofuranose and β-L-ido-heptofuranose;

1,2-O-isopropylidene-3-O-(2-methylnaphthylmethyl)-5-O-chloroacetyl-6,7-dideoxy-α-D-gluco-heptofuranose and β-L-ido-heptofuranose;

1,2-O-isopropylidene-3-O-(2-chloronaphthylmethyl)-5-O-chloroacetyl-6,7-dideoxy-α-D-gluco-heptofuranose and β-L-ido-heptofuranose;

1,2-O-isopropylidene-3-O-(2-bromobenzyl)-5-O-chloroacetyl-6,7-dideoxy-α-D-gluco-heptofuranose and β-L-ido-heptofuranose;

1,2-O-isopropylidene-3-O-(2-fluorobenzyl)-5-O-chloroacetyl-6,7-dideoxy-α-D-gluco-heptofuranose and β-L-ido-heptofuranose;

1,2-O-isopropylidene-3-O-(2-iodobenzyl)-5-O-chloroacetyl-5-O-chloroacetyl-6,7-dideoxy-α-D-gluco-heptofuranose and β-L-ido-heptofuranose;

1,2-O-isopropylidene-3-O-(4-chlorobenzyl)-5-O-chloroacetyl-6,7-dideoxy-α-D-gluco-heptofuranose and β-L-ido-heptofuranose;

1,2-O-isopropylidene-3-O-(3-chlorobenzyl)-5-O-chloroacetyl-6,7-dideoxy-α-D-gluco-heptofuranose and β-L-ido-heptofuranose;

1,2-O-isopropylidene-3-O-(4-methylbenzyl)-5-O-chloroacetyl-6,7-dideoxy-α-D-gluco-heptofuranose and β-L-ido-heptofuranose;

1,2-O-isopropylidene-3-O-(2,3,4-trichlorobenzyl)-5-O-chloroacetyl-6,7-dideoxy-α-D-gluco-heptofuranose and β-L-ido-heptofuranose;

1,2-O-isopropylidene-3-O-(2-chloro-3,4-dimethylbenzyl)-5-O-chloroacetyl-6,7-dideoxy-α-D-gluco-heptofuranose and β-L-ido-heptofuranose;

1,2-O-isopropylidene-3-O-(2-methyl-4-bromobenzyl)-5-O-chloroacetyl-6,7-dideoxy-α-D-gluco-heptofuranose and β-L-ido-heptofuranose;

1,2-O-isopropylidene-3-O-(2-chloro-4-trifluoromethylbenzyl)-5-O-chloroacetyl-6,7-dideoxy-α-D-gluco-heptofuranose and β-L-ido-heptofuranose;

1,2-O-isopropylidene-3-O-(2-chloro-3-bromobenzyl)-5-O-chloroacetyl-6,7-dideoxy-α-D-gluco-heptofuranose and β-L-ido-heptofuranose;

1,2-O-isopropylidene-3-O-(2-butyl-3-fluorobenzyl)-5-O-chloroacetyl-6,7-dideoxy-α-D-gluco-heptofuranose and β-L-ido-heptofuranose;

1,2-O-isopropylidene-3-O-(3,4-dichlorobenzyl)-5-O-chloroacetyl-6,7-dideoxy-α-D-gluco-heptofuranose and β-L-ido-heptofuranose;

1,2-O-isopropylidene-3-O-(3-ethyl-4-bromobenzyl)-5-O-chloroacetyl-6,7-dideoxy-α-D-gluco-heptofuranose and β-L-ido-heptofuranose;

1,2-O-isopropylidene-3-O-(3-butyl-4-butylbenzyl)-5-O-chloroacetyl-6,7-dideoxy-α-D-gluco-heptofuranose and β-L-ido-heptofuranose;

1,2-O-isopropylidene-3-O-(2-chlorobenzyl)-5-O-chloroacetyl-6-deoxy-α-D-glucofuranose and β-L-idofuranose;

1,2-O-isopropylidene-3-O-(2-methylbenzyl)-5-O-chloroacetyl-6-deoxy-α-D-glucofuranose and β-L-idofuranose;

1,2-O-isopropylidene-3-O-(naphthylmethyl)-5-O-chloroacetyl-6-deoxy-α-D-glucofuranose and β-L-idofuranose;

1,2-O-isopropylidene-3-O-(2-methylnaphthylmethyl)-5-O-chloroacetyl-6-deoxy-α-D-glucofuranose and β-L-ido-furanose;

1,2-O-isopropylidene-3-O-(2-chloronaphthylmethyl)-5-O-chloroacetyl-6-deoxy-α-D-glucofuranose and β-L-ido-furanose;

1,2-O-isopropylidene-3-O-(2-bromobenzyl)-5-O-chloroacetyl-6-deoxy-α-D-glucofuranose and β-L-idofuranose;

1,2-O-isopropylidene-3-O-(2-fluorobenzyl)-5-O-chloroacetyl-6-deoxy-α-D-glucofuranose and β-L-idofuranose;

1,2-O-isopropylidene-3-O-(2-iodobenzyl)-5-O-chloroacetyl-6-deoxy-α-D-glucofuranose and β-L-idofuranose;

1,2-O-isopropylidene-3-O-(4-chlorobenzyl)-5-O-chloroacetyl-6-deoxy-α-D-glucofuranose and β-L-idofuranose;

1,2-O-isopropylidene-3-O-(3-chlorobenzyl)-5-O-chloroacetyl-6-deoxy-α-D-glucofuranose and β-L-idofuranose;

1,2-O-isopropylidene-3-O-(4-methylbenzyl)-5-O-chloroacetyl-6-deoxy-α-D-glucofuranose and β-L-idofuranose;

1,2-O-isopropylidene-3-O-(2,3,4-trichlorobenzyl)-5-O-chloroacetyl-6-deoxy-α-D-glucofuranose and β-L-idofuranose;

1,2-O-isopropylidene-3-O-(2-chloro-3,4-dimethylbenzyl)-5-O-chloroacetyl-6-deoxy-α-D-glucofuranose and β-L-idofuranose;

1,2-O-isopropylidene-3-O-(2-methyl-4-bromobenzyl)-5-O-chloroacetyl-6-deoxy-α-D-glucofuranose and β-L-ido-furanose;

1,2-O-isopropylidene-3-O-(2-chloro-4-trifluoromethylbenzyl)-5-O-chloroacetyl-6-deoxy-α-D-glucofuranose and β-L-idofuranose;

1,2-O-isopropylidene-3-O-(2-chloro-3-bromobenzyl)-5-O-chloroacetyl-6-deoxy-α-D-glucofuranose and β-L-ido-furanose;

1,2-O-isopropylidene-3-O-(2-butyl-3-fluorobenzyl)-5-O-chloroacetyl-6-deoxy-α-D-glucofuranose and β-L-ido-furanose;

1,2-O-isopropylidene-3-O-(3,4-dichlorobenzyl)-5-O-chloroacetyl-6-deoxy-α-D-glucofuranose and β-L-ido-furanose;

1,2-O-isopropylidene-3-O-(3-ethyl-4-bromobenzyl)-5-O-chloroacetyl-6-deoxy-α-D-glucofuranose and β-L-ido-furanose;

1,2-O-isopropylidene-3-O-(3-butyl-4-butylbenzyl)-5-O-chloroacetyl-6-deoxy-α-D-glucofuranose and β-L-ido-furanose;

1,2-O-isopropylidene-3-O-(2-chlorobenzyl)-5-O-chloroacetyl-6,7,8-trideoxy-α-D-gluco-octofuranose and β-L-ido-octofuranose;

1,2-O-isopropylidene-3-O-(2-methylbenzyl)-5-O-chloroacetyl-6,7,8-trideoxy-α-D-gluco-octofuranose and β-L-ido-octofuranose;

1,2-O-isopropylidene-3-O-(naphthylmethyl)-5-O-chloroacetyl-6,7,8-trideoxy-α-D-gluco-octofuranose and β-L-idooctofuranose;

1,2-O-isopropylidene-3-O-(2-methylnaphthylmethyl)-5-O-chloroacetyl-6,7,8-trideoxy-α-D-gluco-octofuranose and β-L-ido-octofuranose;

1,2-O-isopropylidene-3-O-(2-chloronaphthylmethyl)-5-O-chloroacetyl-6,7,8-trideoxy-α-D-gluco-octofuranose and β-L-iodo-octofuranose;

1,2-O-isopropylidene-3-O-(2-bromobenzyl)-5-O-chloroacetyl-6,7,8-trideoxy-α-D-gluco-octofuranose and β-L-ido-octofuranose;

1,2-O-isopropylidene-3-O-(2-fluorobenzyl)-5-O-chloroacetyl-6,7,8-trideoxy-α-D-gluco-octofuranose and β-L-ido-octofuranose;

1,2-O-isopropylidene-3-O-(2-iodobenzyl)-5-O-chloroacetyl-6,7,8-trideoxy-α-D-gluco-octofuranose and β-L-ido-octofuranose;

1,2-O-isopropylidene-3-O-(4-chlorobenzyl)-5-O-chloroacetyl-6,7,8-trideoxy-α-D-gluco-octofuranose and β-L-ido-octofuranose;

1,2-O-isopropylidene-3-O-(3-chlorobenzyl)-5-O-chloroacetyl-6,7,8-trideoxy-α-D-gluco-octofuranose and β-L-ido-octofuranose;

1,2-O-isopropylidene-3-O-(4-methylbenzyl)-5-O-chloroacetyl-6,7,8-trideoxy-α-D-gluco-octofuranose and β-L-ido-octofuranose;

1,2-O-isopropylidene-3-O-(2,3,4-trichlorobenzyl)-5-O-chloroacetyl-6,7,8-trideoxy-α-D-gluco-octofuranose and β-L-ido-octofuranose;

1,2-O-isopropylidene-3-O-(2-chloro-3,4-dimethylbenzyl)-5-O-chloroacetyl-6,7,8-trideoxy-α-D-gluco-octo-furanose and β-L-ido-octofuranose;

1,2-O-isopropylidene-3-O-(2-methyl-4-bromobenzyl)-5-O-chloroacetyl-6,7,8-trideoxy-α-D-gluco-octofuranose and β-L-ido-octofuranose;

1,2-O-isopropylidene-3-O-(2-chloro-4-trifluoromethylbenzyl)-5-O-chloroacetyl-6,7,8-trideoxy-α-D-gluco-octofuranose and β-L-ido-octofuranose;

1,2-O-isopropylidene-3-O-(2-chloro-3-bromobenzyl)-5-O-chloroacetyl-6,7,8-trideoxy-α-D-gluco-octofuranose and β-L-ido-octofuranose;

1,2-O-isopropylidene-3-O-(2-butyl-3-fluorobenzyl)-5-O-chloroacetyl-6,7,8-trideoxy-α-D-gluco-octofuranose and β-L-ido-octofuranose;

1,2-O-isopropylidene-3-O-(3,4-dichlorobenzyl)-5-O-chloroacetyl-6,7,8-trideoxy-α-D-gluco-octofuranose and β-L-ido-octofuranose;

1,2-O-isopropylidene-3-O-(3-ethyl-4-bromobenzyl)-5-O-chloroacetyl-6,7,8-trideoxy-α-D-gluco-octofuranose and β-L-ido-octofuranose; and 1,2-O-isopropylidene-3-O-(3-butyl-4-butylbenzyl)-5-O-chloroacetyl-6,7,8-trideoxy-α-D-gluco-octofuranose and β-L-ido-octofuranose;

1,2-O-isopropylidene-3-O-(2-chlorobenzyl)-5-C-butyl-5-O-chloroacetyl-α-D-gluco-pentofuranose and β-L-ido-pentofuranose;

1,2-O-isopropylidene-3-O-(2-methylbenzyl)-5-C-butyl-5-O-chloroacetyl-α-D-gluco-pentofuranose and β-L-ido-pentofuranose;

1,2-O-isopropylidene-3-O-(naphthylmethyl)-5-C-butyl-5-O-chloroacetyl-α-D-gluco-pentofuranose and β-L-ido-pentofuranose;

1,2-O-isopropylidene-3-O-(2-methylnaphthylmethyl)-5-C-butyl-5-O-chloroacetyl-α-D-gluco-pentofuranose and β-L-ido-pentofuranose;

1,2-O-isopropylidene-3-O-(2-chloronaphthylmethyl)-5-C-butyl-5-O-chloroacetyl-α-D-gluco-pentofuranose and β-L-ido-pentofuranose;

1,2-O-isopropylidene-3-O-(2-bromobenzyl)-5-C-butyl-5-O-chloroacetyl-α-D-gluco-pentofuranose and β-L-ido-pentofuranose;

1,2-O-isopropylidene-3-O-(2-fluorobenzyl)-5-C-butyl-5-O-chloroacetyl-α-D-gluco-pentofuranose and β-L-ido-pentofuranose;

1,2-O-isopropylidene-3-O-(2-iodobenzyl)-5-C-butyl-5-O-chloroacetyl-α-D-gluco-pentofuranose and β-L-ido-pentofuranose;

1,2-O-isopropylidene-3-O-(4-chlorobenzyl)-5-C-butyl-5-O-chloroacetyl-α-D-gluco-pentofuranose and β-L-ido-pentofuranose;

1,2-O-isopropylidene-3-O-(3-chlorobenzyl)-5-C-butyl-5-O-chloroacetyl-α-D-gluco-pentofuranose and β-L-ido-pentofuranose;

1,2-O-isopropylidene-3-O-(4-methylbenzyl)-5-C-butyl-5-O-chloroacetyl-α-D-gluco-pentofuranose and β-L-ido-pentofuranose;

1,2-O-isopropylidene-3-O-(2,3,4-trichlorobenzyl)-5-C-butyl-5-O-chloroacetyl-α-D-gluco-pentofuranose and β-L-ido-pentofuranose;

1,2-O-isopropylidene-3-O-(2-chloro-3,4-dimethylbenzyl)-5-C-butyl-5-O-chloroacetyl-α-D-gluco-pentofuranose and β-L-ido-pentofuranose;

1,2-O-isopropylidene-3-O-(2-methoxy-4-bromobenzyl)-5-C-butyl-5-O-chloroacetyl-α-D-gluco-pentofuranose and β-L-ido-pentofuranose;

1,2-O-isopropylidene-3-O-(2-chloro-4-trifluoromethylbenzyl)-5-C-butyl-5-O-chloroacetyl-α-D-gluco-pentofuranose and β-L-ido-pentofuranose;

1,2-O-isopropylidene-3-O-(2-chloro-3-bromobenzyl)-5-C-butyl-5-O-chloroacetyl-α-D-gluco-pentofuranose and β-L-ido-pentofuranose;

1,2-O-isopropylidene-B 3-O-(2-butyl-3-fluorobenzyl)-5-C-butyl-5-O-chloroacetyl-α-D-gluco-pentofuranose and β-L-ido-pentofuranose;

1,2-O-isopropylidene-3-O-(3,4-dichlorobenzyl)-5-C-butyl-5-O-chloroacetyl-α-D-gluco-pentofuranose and β-L-ido-pentofuranose;

1,2-O-isopropylidene-3-O-(3-ethyl-4-bromobenzyl)-5-C-butyl-5-O-chloroacetyl-α-D-gluco-pentofuranose and β-L-ido-pentofuranose; and 1,2-O-isopropylidene-3-O-(3-butyl-4-butylbenzyl)-5-C-butyl-5-O-chloroacetyl-α-D-gluco-pentofuranose and β-L-ido-pentofuranose;

1,2-O-isopropylidene-3-O-(2-chlorobenzyl)-5-O-chloroacetyl-5-C-methyl-6,7-dideoxy-α-D-gluco-heptofuranose and β-L-iodo-heptofuranose;

1,2-O-isopropylidene-3-O-(2-bromobenzyl)-5-O-chloroacetyl-5-C-methyl-6,7-dideoxy-α-D-gluco-heptofuranose and β-L-ido-heptofuranose;

1,2-O-isopropylidene-3-O-(4-methylbenzyl)-5-O-chloroacetyl-5-C-methyl-6,7-dideoxy-α-D-gluco-heptofuranose and β-L-ido-heptofuranose;

1,2-O-isopropylidene-3-O-(2-chloro-3-bromobenzyl)-5-O-chloroacetyl-5-C-methyl-6,7-dideoxy-α-D-gluco-heptofuranose and β-L-ido-heptofuranose;

1,2-O-isopropylidene-3-O-(2-chlorobenzyl)-5-O-chloroacetyl-5-C-methyl-6-deoxy-α-D-glucofuranose and β-L-idofuranose;

1,2-O-isopropylidene-3-O-(2-bromobenzyl)-5-O-chloroacetyl-5-C-methyl-6-deoxy-α-D-glucofuranose and β-L-ido-furanose;

1,2-O-isopropylidene-3-O-(2-methylbenzyl)-5-O-chloroacetyl-5-C-methyl-6-deoxy-α-D-glucofuranose and β-L-ido-furanose;

1,2-O-isopropylidene-3-O-(2-chloro-3-bromobenzyl)-5-O-chloroacetyl-5-C-methyl-6-deoxy-α-D-glucofuranose and β-L-idofuranose;

1,2-O-isopropylidene-3-O-(2-chlorobenzyl)-5-O-chloroacetyl-5-C-methyl-6,7,8-trideoxy-α-D-gluco-octofuranose and β-L-ido-octofuranose;

1,2-O-isopropylidene-3-O-(2-bromobenzyl)-5-O-chloroacetyl-5-C-methyl-6,7,8-trideoxy-α-D-gluco-octofuranose and β-L-ido-octofuranose;

1,2-O-isopropylidene-3-O-(4-methylbenzyl)-5-O-chloroacetyl-5-C-methyl-6,7,8-trideoxy-α-D-gluco-octofuranose and β-L-ido-octofuranose;

1,2-O-isopropylidene-3-O-(2-chloro-3-bromobenzyl)-5-O-chloroacetyl-6,7,8-trideoxy-α-D-gluco-octofuranose and β-L-ido-octofuranose;

1,2-O-isopropylidene-3-O-(2-chlorobenzyl)-5-C-butyl-5-O-chloroacetyl-5-C-methyl-α-D-gluco-pentofuranose and β-L-ido-pentofuranose;

1,2-O-isopropylidene-3-O-(2-bromobenzyl)-5-C-butyl-5-O-chloroacetyl-5-C-methyl-α-D-gluco-pentofuranose and β-L-ido-pentofuranose;

1,2-O-isopropylidene-3-O-(4-methylbenzyl)-5-C-butyl-5-O-chloroacetyl-5-C-methyl-α-D-gluco-pentofuranose and β-L-ido-pentofuranose;

1,2-O-isopropylidene-3-O-(2-chloro-3-bromobenzyl)-5-C-butyl-5-O-chloroacetyl-5-C-methyl-α-D-glucopentofuranose and β-L-ido-pentofuranose;

1,2-O-isopropylidene-3-O-(2-chlorobenzyl)-5-O-chloroacetyl-5-C-methyl-6,7,8-trideoxy-α-D-gluco-octofuranose and β-L-ido-octofuranose;

1,2-O-(2-methylpropylidene)-3-O-(2-chlorobenzyl)-5-O-chloroacetyl-6,7-dideoxy-α-O-gluco-heptofuranose and β-L-iodo-heptofuranose;

1,2-O-(2-methylpropylidene)-3-O-(2-fluorobenzyl)-5-O-chloroacetyl-6,7-dideoxy-α-D-gluco-heptofuranose and β-L-ido-heptofuranose;

1,2-O-(2-methylpropylidene)-3-O-(2-chloro-3,4-dimethylbenzyl)-5-O-chloroacetyl-6,7-dideoxy-α-D-glucoheptofuranose and β-L-ido-heptofuranose;

1,2-O-(2-methylpropylidene)-3-O-(3-ethyl-4-bromobenzyl)-5-O-chloroacetyl-6,7-dideoxy-α-D-gluco-heptofuranose and β-L-ido-heptofuranose;

1,2-O-(2-methylpropylidene)-3-O-(3-ethyl-4-bromobenzyl)-5-O-chloroacetyl-6,7-dideoxy-α-D-gluco-heptofuranose and β-L-ido-heptofuranose;

1,2-O-(2-methylpropylidene)-3-O-(4-methylbenzyl)-5-O-chloroacetyl-6-deoxy-α-D-glucofuranose and β-L-ido-furanose;

1,2-O-(2-methylpropylidene)-3-O-(2-butyl-3-fluorobenzyl)-5-O-chloroacetyl-6-deoxy-α-D-glucofuranose and β-L-idofuranose;

1,2-O-(2-methylpropylidene)-3-O-(naphthylmethyl)-5-O-chloroacetyl-6,7,8-trideoxy-α-D-gluco-octofuranose and β-L-ido-octofuranose;

1,2-O-(2-methylpropylidene)-3-O-(4-chlorobenzyl)-5-O-chloroacetyl-6,7,8-trideoxy-α-D-gluco-octofuranose and β-L-ido-octofuranose;

1,2-O-(2-methylpropylidene)-3-O-(2-chloro-4-trifluoromethylbenzyl)-5-O-chloroacetyl-6,7,8-trideoxy-α-D-gluco-octofuranose and β-L-ido-octofuranose;

1,2-O-(2-methylpropylidene)-3-O-(2-chlorobenzyl)-5-C-butyl-5-O-chloroacetyl-α-D-gluco-pentofuranose and β-L-ido-pentofuranose;

1,2-O-(2-methylpropylidene)-3-O-(2-fluorobenzyl)-5-C-butyl-5-O-chloroacetyl-α-D-gluco-pentofuranose and β-L-ido-pentofuranose;

1,2-O-(2-methylpropylidene)-3-O-(2-chloro-3,4-dimethylbenzyl)-5-C-butyl-5-O-chloroacetyl-α-D-gluco-pentofuranose and β-L-ido-pentofuranose;

1,2-O-methylene-3-O-(2-chlorobenzyl)-5-O-chloroacetyl-6,7-dideoxy-α-D-gluco-heptofuranose and β-L-iodo-heptofuranose;

1,2-O-methylene-3-O-(4-chlorobenzyl)-5-O-chloroacetyl-6,7-dideoxy-α-D-gluco-heptofuranose and β-L-ido-heptofuranose;

1,2-O-methylene-3-O-(2-butyl-3-fluorobenzyl)-5-O-chloroacetyl-6,7-dideoxy-α-D-gluco-heptofuranose and β-L-ido-heptofuranose;

1,2-O-methylene-3-O-(2-chloronaphthylmethyl)-5-O-chloroacetyl-6-deoxy-α-D-glucofuranose and β-L-ido-furanose;

1,2-O-methylene-3-O-(2-chloro-3,4-dimethylbenzyl)-5-O-chloroacetyl-6-deoxy-α-D-glucofuranose and β-L-ido-furanose;

1,2-O-methylene-3-O-(2-chlorobenzyl)-5-O-chloroacetyl-6,7,8-trideoxy-α-D-gluco-octofuranose and β-L-ido-octofuranose;

1,2-O-methylene-3-O-(4-chlorobenzyl)-5-O-chloroacetyl-6,7,8-trideoxy-α-D-gluco-octofuranose and β-L-ido-octofuranose;

1,2-O-methylene-3-O-(2-butyl-3-fluorobenzyl)-5-O-chloroacetyl-6,7,8-trideoxy-α-D-gluco-octofuranose and β-L-ido-octofuranose;

1,2-O-methylene-3-O-(2-chloronaphthylmethyl)-5-C-butyl-5-O-chloroacetyl-α-D-gluco-pentofuranose and β-L-ido-pentofuranose;

1,2-O-methylene-3-O-(2-chloro-3,4-dimethylbenzyl)-5-C-butyl-5-O-chloroacetyl-α-D-gluco-pentofuranose and β-L-ido-pentofuranose.

Similarly, by applying the same procedure but respectively using acetic anhydride, benzoyl chloride, 2-chlorobenzoyl chloride, methoxyacetyl chloride, 2-trifluoromethylbenzoyl chloride, 4-methoxybenzoyl chloride, 2,4-difluorobenzoyl, 2-methyl-3-chlorobenzoyl chloride and in place of chloroacetyl chloride, the corresponding 5-O-acetyl; 5-O-benzoyl; 5-O-2'-chlorobenzoyl; 5-O-methoxyacetyl; 5-O-2'-trifluoromethylbenzoyl-O-; 5-O-4'-methoxybenzoyl; 5-O-2',4'-difluorobenzoyl, and 5-O-(2-methyl-3-chlorobenzoyl)- analogs of the products of Examples 4 and 8 can be prepared.

EXAMPLE 10

By applying the appropriate procedures described in the above examples and the appropriate starting materials, the compounds listed in the following Tables hereinbelow were prepared.

PRE-EMERGENT HERBICIDE TEST

Pre-emergence herbicidal activity was determined in the following manner.

Test solutions of the respective compounds were prepared as follows:

355.5 mg of test compound was dissolved in 15 ml of acetone. 2 ml of acetone containing 110 mg of a nonionic surfactant was added to the solution. 12 ml of this stock solution was then added to 47.7 ml of water which contained the same nonionic surfactant at a concentration of 625 mg/l.

Seeds of the test vegetation were planted in a pot of soil and the test solution was sprayed uniformly onto the soil surface at a dose of 27.5 micrograms/cm². The pot was watered and placed in a greenhouse. The pot was watered intermittently and observed for seedling emergence, health of emerging seedlings, etc., for a 3-week period. At the end of this period, the herbicidal effectiveness of the compound was rated based on the physiological observations. A 0- to 100-scale was used, 0 representing no phytotoxicity, 100 representing complete kill. The results of these tests are summarized in Table 1.

POST-EMERGENT HERBICIDAL TEST

The test compound was formulated in the same manner as described above for the pre-emergent test. This formulation was uniformly sprayed on 2 similar pots containing plants 2 to 3 inches tall (except wild oats, soybean and watergrass which were 3 to 4 inches tall) (approximately 15 to 25 plants per pot) at a dose of 27.5 microgram/cm². After the plants had dried, they were placed in a greenhouse and then watered intermittently at their bases as needed. The plants were observed periodically for phytotoxic effects and physiological and morphological responses to the treatment. After 3 weeks, the herbicidal effectiveness of the compound was rated based on these observations. A 0- to 100-scale was used, 0 representing no phytotoxicity, 100 representing complete kill. The results of these tests are summarized in Table 2.

TABLE A

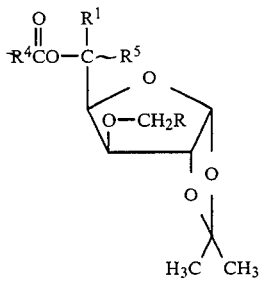

| No. | R | $R^1$ | $R^4$ | $R^5$ | Carbon Calc. | Carbon Found | Hydrogen Calc. | Hydrogen Found | Melt. Point °C. |
|---|---|---|---|---|---|---|---|---|---|
| 1 | 2-Clφ—* | $CH_3CH_2$— | $CH_3$= | H | 59.3 | 59.62 | 6.55 | 6.62 | liquid |
| 2 | 2-Clφ— | $CH_3$— | $CH_3$— | H | 58.3 | 58.97 | 6.25 | 6.32 | liquid |
| 3 | 2-Clφ— | $CH_3CH_2$ | $ClCH_2$ | H | 54.43 | 52.57 | 5.77 | 5.7 | liquid |
| 4 | 2-Clφ— | $CH_3$ | φ | H | 63.82 | 63.81 | 5.82 | 5.97 | liquid |
| 5 | 2-Clφ— | $CH_3$— | 2-Clφ | H | 59.11 | 59.00 | 5.18 | 5.34 | 119–122 |
| 6 | 2-Clφ— | $CH_3$— | $CH_3$— | $CH_3$— | 59.29 | 58.80 | 6.55 | 6.52 | liquid |
| 7 | 2-$CH_3$φ— | $CH_3$ | φ | H | 69.88 | 72.23 | 6.84 | 7.47 | 96–99 |
| 8 | 2-Clφ— | $CH_3$ | $CH_3OCH_2$ | H | 56.93 | 56.79 | 6.29 | 6.14 | liquid |

*φ = phenyl; for example, 2-Clφ = 2-chlorophenyl

EXAMPLE 11

In this example, the compounds of Table A were respectively tested using the procedures described hereinbelow for pre-emergent and post-emergent activity against a variety of grasses and broad-leaf plants including one grain crop and one broad-leaf crop. The compounds tested are identified by compound number in Tables A and B hereinabove.

TABLE 1

| | Pre-Emergence Herbicidal Activity | | | | | | | |
|---|---|---|---|---|---|---|---|---|
| | Broad-Leaf Plants % Phytotoxicity | | | | Grasses % Phytotoxicity | | | |
| Compound No. | Lambs Quarter | Mustard | Pigweed | Soybean | Crab Grass | Water Grass | Wild Oats | Rice |
| 1 | 50 | 40 | 30 | 28 | 98 | 100 | 70 | 93 |
| 2 | 25 | 0 | 10 | 25 | 100 | 95 | 20 | 50 |
| 3 | 0 | 0 | 0 | 0 | 100 | 100 | 0 | 30 |
| 4 | 30 | 0 | 20 | 0 | 90 | 90 | 90 | 40 |
| 5 | 0 | 0 | 0 | 0 | 25 | 0 | 0 | 0 |
| 6 | 40 | 30 | 30 | 25 | 100 | 93 | 25 | 85 |
| 7 | 70 | 55 | 60 | 75 | 90 | 85 | 75 | 75 |
| 8 | 70 | 65 | 75 | 70 | 100 | 95 | 85 | 85 |

TABLE 2

| | Post-Emergence Herbicidal Activity | | | | | | | |
|---|---|---|---|---|---|---|---|---|
| | Broad-Leaf Plants % Phytotoxicity | | | | Grasses % Phytotoxicity | | | |
| Compound No. | Lambs Quarter | Mustard | Pigweed | Soybean | Crab Grass | Water Grass | Wild Oats | Rice |
| 1 | 0 | 0 | 0 | 0 | 30 | 75 | 15 | 0 |
| 2 | 0 | 0 | 0 | 0 | 0 | 0 | 0 | 30 |
| 3 | 0 | 0 | 0 | 0 | 0 | 0 | 0 | 0 |
| 4 | 0 | 0 | 0 | 0 | 20 | 0 | 0 | 0 |
| 5 | 0 | 0 | 0 | 0 | 0 | 0 | 0 | 0 |
| 6 | 0 | 0 | 0 | 0 | 0 | 0 | 0 | 5 |
| 7 | 0 | 0 | 0 | 0 | 35 | 35 | 0 | 0 |
| 8 | 0 | 0 | 0 | 0 | 20 | 25 | 10 | 25 |

Obviously, many modifications and variations of the invention described hereinabove and below in the claims can be made without departing from the essence and scope thereof.

What is claimed is:

1. A compound having the formula:

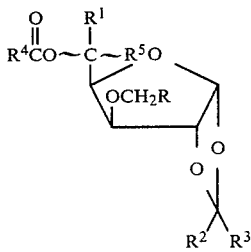

wherein
the wavy (∼) bond line indicates the D-gluco or L-ido isomers or mixtures thereof,
R is naphthyl, 2-trifluoromethylphenyl, or substituted aryl having 6 through 10 ring carbon atoms and 1 through 3 substituents independently selected from the group of lower alkyl, and halo;
$R^1$ is alkyl having 1 through 4 carbon atoms;
$R^2$ and $R^3$ are independently selected from the group consisting of hydrogen, lower alkyl, lower haloalkyl having 1 through 3 halo substituents and aryl having 6 through 10 carbon atoms or $R^2$ and $R^3$ together with the carbon atom to which they are joined form a cycloalkyl group having 5 or 6 carbon atoms;
$R^4$ is lower alkyl, lower alkoxyalkyl, lower haloalkyl having 1 through 3 halo substituents, aryl having 6 through 10 ring carbon atoms or substituted aryl having 1 through 3 substituents selected from the group of lower alkyl, lower alkoxy, and trifluoromethyl; and
$R^5$ is hydrogen or methyl.

2. The compound of claim 1 wherein $R^5$ is hydrogen.
3. The compound of claim 1 wherein $R^1$ is methyl.
4. The compound of claim 1 wherein $R^1$ is ethyl.
5. The compound of claim 1 wherein $R^4$ is lower alkyl; lower halo alkyl or phenyl.
6. The compound of claim 1 wherein R is 2-trifluoromethylphenyl; 2-lower alkylphenyl; or 2-halophenyl.
7. The compound of claim 6 wherein R is 2-halophenyl.
8. The compound of claim 7 wherein R is 2-chlorophenyl.
9. The compound of claim 8 wherein $R^1$ is methyl.
10. The compound of claim 9 wherein $R^2$ is methyl and $R^3$ is methyl and $R^4$ is lower alkyl, haloalkyl or phenyl.
11. The compound of claim 8 wherein $R^1$ is ethyl.
12. The compound of claim 11 wherein $R^2$ is methyl and $R^3$ is methyl and $R^4$ is lower alkyl, haloalkyl or phenyl.
13. The compound of claim 12 wherein $R^4$ is methyl or chloromethyl.
14. The compound of claim 10 wherein $R^4$ is methyl or chloromethyl.
15. An herbicidal composition comprising an herbicidally effective amount of a compound according to claim 1 effective to reduce the growth of green plants, and a compatible carrier.
16. A method for treating undesired vegetation which comprises supplying an herbicidally effective amount of a compound of claim 13 to the foliage or growth medium of said vegetation.
17. A method for treating undesired grasses which comprises applying an herbicidally effective amount of the compound of claim 9 to the foliage or growth medium of said grasses.
18. A plant growth regulating composition comprising a compatible carrier and a plant growth regulating effective amount of a compound according to claim 1.
19. A method for regulating plant growth which comprises applying a plant growth regulating effective amount of the compound of claim 1 to the foliage or growth medium of said plants.
20. A pre-emergence herbicidal composition comprising a pre-emergence herbicidally effective amount of a compound according to claim 1 effective when applied to the growth medium of grasses to prevent or reduce the germination or early growth of grasses.

* * * * *

UNITED STATES PATENT AND TRADEMARK OFFICE
CERTIFICATE OF CORRECTION

PATENT NO. : 4,497,649
DATED : February 5, 1985
INVENTOR(S) : WILLIAM LOH

It is certified that error appears in the above–identified patent and that said Letters Patent are hereby corrected as shown below:

Col. 8, line 61, "to the following point" should read --to the boiling point--

Signed and Sealed this

Second Day of July 1985

[SEAL]

Attest:

DONALD J. QUIGG

*Attesting Officer*    *Acting Commissioner of Patents and Trademarks*